United States Patent
Brady et al.

[11] Patent Number: 6,127,333
[45] Date of Patent: Oct. 3, 2000

[54] CONJUGATES USEFUL IN THE TREATMENT OF PROSTATE CANCER

[75] Inventors: Stephen F. Brady, Philadelphia; Victor M. Garsky, Blue Bell; Joseph M. Pawluczyk, Plymouth Meeting, all of Pa.

[73] Assignee: Merck & Co., Inc., Rahway, N.J.

[21] Appl. No.: 09/112,656

[22] Filed: Jul. 9, 1998

Related U.S. Application Data

[60] Provisional application No. 60/052,195, Jul. 10, 1997.

[51] Int. Cl.⁷ ...................................................... A61K 38/00
[52] U.S. Cl. .................................. 514/2; 514/16; 514/17; 514/18; 530/329; 530/330; 540/478
[58] Field of Search ..................................... 530/329, 330; 514/2, 16, 17, 18; 540/478

[56] References Cited

U.S. PATENT DOCUMENTS

| | | | |
|---|---|---|---|
| 4,203,898 | 5/1980 | Cullinan et al. | 260/244.4 |
| 4,388,305 | 6/1983 | Trouet et al. | . |
| 4,703,107 | 10/1987 | Monsigny et al. | 530/330 |
| 4,828,831 | 5/1989 | Hannart et al. | 424/85.91 |
| 4,870,162 | 9/1989 | Trouet et al. | 530/363 |
| 5,024,835 | 6/1991 | Rao et al. | 424/85.91 |
| 5,030,620 | 7/1991 | Hannart et al. | 514/18 |
| 5,349,066 | 9/1994 | Kaneko et al. | 546/294 |
| 5,502,037 | 3/1996 | Kondratyev | 514/21 |
| 5,599,686 | 2/1997 | DeFeo-Jones et al. | 435/23 |

FOREIGN PATENT DOCUMENTS

| | | |
|---|---|---|
| 0 126 344 A2 | 11/1984 | European Pat. Off. . |
| 0 647 450 A1 | 4/1995 | European Pat. Off. . |
| WO96/05863 | 2/1996 | WIPO . |

OTHER PUBLICATIONS

J. Med. Chem, vol. 26, No. 5, pp. 638–644 (1983), by P. K. Chakravarty, et al.

J. Med. Chem., vol. 26, No. 5, pp. 633–638 (1983), by P. K. Chakravarty, et al.

J. Med. Chem, vol. 21, No. 1, pp. 88–96 (1978), by C. J. Barnett, et al.

*Primary Examiner*—Dwayne C. Jones
*Assistant Examiner*—C. Delacroix-Muirheid
*Attorney, Agent, or Firm*—David A. Muthard; Mark R. Daniel

[57] ABSTRACT

Chemical conjugates which comprise oligopeptides, having amino acid sequences that are selectively proteolytically cleaved by free prostate specific antigen (PSA) and known cytotoxic agents are disclosed. The conjugates of the invention are characterized by a diamine linker between the oligopeptide and vinblastine. Such conjugates are useful in the treatment of prostatic cancer and benign prostatic hypertrophy (BPH).

21 Claims, No Drawings

CONJUGATES USEFUL IN THE TREATMENT OF PROSTATE CANCER

The instant application claims priority to Provisional Application No. 60/052,195, filed Jul. 10, 1997.

BACKGROUND OF THE INVENTION

In 1996 cancer of the prostate gland was expected to be diagnosed in 317,000 men in the U.S. and 42,000 American males die from this disease (Garnick, M. B. (1994). The Dilemmas of Prostate Cancer. Scientific American, April:72–81). Thus, prostate cancer is the most frequently diagnosed malignancy (other than that of the skin) in U.S. men and the second leading cause of cancer-related deaths (behind lung cancer) in that group.

Prostate specific Antigen (PSA) is a single chain 33 kDa glycoprotein that is produced almost exclusively by the human prostate epithelium and occurs at levels of 0.5 to 2.0 mg/ml in human seminal fluid (Nadji, M., Taber, S. Z., Castro, A., et al. (1981) Cancer 48:1229; Papsidero, L., Kuriyama, M., Wang, M., et al. (1981). JNCI 66:37; Qui, S. D., Young, C. Y. F., Bihartz, D. L., et al. (1990), J. Urol. 144:1550; Wang, M. C., Valenzuela, L. A., Murphy, G. P., et al. (1979). Invest. Urol. 17:159). The single carbohydrate unit is attached at asparagine residue number 45 and accounts for 2 to 3 kDa of the total molecular mass. PSA is a protease with chymotrypsin-like specificity (Christensson, A., Laurell, C. B., Lilja, H. (1990). Eur. J. Biochem. 194:755–763). It has been shown that PSA is mainly responsible for dissolution of the gel structure formed at ejaculation by proteolysis of the major proteins in the sperm entrapping gel, Semenogelin I and Semenogelin II, and fibronectin (Lilja, H. (1985). J. Clin. Invest. 76:1899; Lilja, H., Oldbring, J., Rannevik, G., et al. (1987). J. Clin. Invest. 80:281; McGee, R. S., Herr, J. C. (1988). Biol. Reprod. 39:499). The PSA mediated proteolysis of the gel-forming proteins generates several soluble Semenogelin I and Semenogelin II fragments and soluble fibronectin fragments with liquefaction of the ejaculate and release of progressively motile spermatoza (Lilja, H., Laurell, C. B. (1984). Scand. J. Clin. Lab. Invest. 44:447; McGee, R. S., Herr, J. C. (1987). Biol. Reprod. 37:431). Furthermore, PSA may proteolytically degrade IGFBP-3 (insulin-like growth factor binding protein 3) allowing IGF to stimulate specifically the growth of PSA secreting cells (Cohen et al., (1992) J. Clin. Endo. & Meta. 75:1046–1053).

PSA complexed to alpha 1-antichymotrypsin is the predominant molecular form of serum PSA and may account for up to 95% of the detected serum PSA (Christensson, A., Björk, T., Nilsson, O., et al. (1993). J. Urol. 150:100–105; Lilja, H., Christensson, A., Dahlén, U. (1991). Clin. Chem. 37:1618–1625; Stenman, U. H., Leinoven, J., Alfthan, H., et al. (1991). Cancer Res. 51:222–226). The prostatic tissue (normal, benign hyperplastic, or malignant tissue) is implicated to predominantly release the mature, enzymatically active form of PSA, as this form is required for complex formation with alpha 1-antichymotrypsin (Mast, A. E., Enghild, J. J., Pizzo, S. V., et al. (1991). Biochemistry 30:1723–1730; Perlmutter, D. H., Glover, G. I., Rivetna, M., et al. (1990). Proc. Natl. Acad. Sci. USA 87:3753–3757). Therefore, in the microenvironment of prostatic PSA secreting cells the PSA is believed to be processed and secreted in its mature enzymatically active form not complexed to any inhibitory molecule. PSA also forms stable complexes with alpha 2-macroglobulin, but as this results in encapsulation of PSA and complete loss of the PSA epitopes, the in vivo significance of this complex formation is unclear. A free, noncomplexed form of PSA constitutes a minor fraction of the serum PSA (Christensson, A., Björk, T., Nilsson, O., et al. (1993). J. Urol. 150:100–105; Lilja, H., Christensson, A., Dahlén, U. (1991). Clin. Chem. 37:1618–1625). The size of this form of serum PSA is similar to that of PSA in seminal fluid (Lilja, H., Christensson, A., Dahlén, U. (1991). Clin. Chem. 37:1618–625) but it is yet unknown as to whether the free form of serum PSA may be a zymogen; an internally cleaved, inactive form of mature PSA; or PSA manifesting enzyme activity. However, it seems unlikely that the free form of serum PSA manifests enzyme activity, since there is considerable (100 to 1000 fold) molar excess of both unreacted alpha 1-antichymotrypsin and alpha 2-macroglobulin in serum as compared with the detected serum levels of the free 33 kDa form of PSA (Christensson, A., Björk, T., Nilsson, O., et al. (1993). J. Urol. 150:100–105; Lilja, H., Christensson, A., Dahlén, U. (1991). Clin. Chem. 37:1618–1625).

Serum measurements of PSA are useful for monitoring the treatment of adenocarcinoma of the prostate (Duffy, M. S. (1989). Ann. Clin. Biochem. 26:379–387; Brawer, M. K. and Lange, P. H. (1989). Urol. Suppl. 5:11–16; Hara, M. and Kimura, H. (1989). J. Lab. Clin. Med. 113:541–548), although above normal serum concentrations of PSA have also been reported in benign prostatic hyperplasia and subsequent to surgical trauma of the prostate (Lilja, H., Christensson, A., Dahlén, U. (1991). Clin. Chem. 37:1618–1625). Prostate metastases are also known to secrete immunologically reactive PSA since serum PSA is detectable at high levels in prostatectomized patients showing widespread metatstatic prostate cancer (Ford, T. F., Butcher, D. N., Masters, R. W., et al. (1985). Brit. J. Urology 57:50–55). Therefore, a cytotoxic compound that could be activated by the proteolytic activity of PSA should be prostate cell specific as well as specific for PSA secreting prostate metastases.

It is the object of this invention to provide a novel anti-cancer composition useful for the treatment of prostate cancer which comprises oligopeptides, that are selectively proteolytically cleaved by free prostate specific antigen (PSA) and that include a cyclic amino acid having a hydrophilic substituent, in conjugation with a cytotoxic agent.

Another object of this invention is to provide a method of treating prostate cancer which comprises administration of the novel anti-cancer composition.

SUMMARY OF THE INVENTION

Chemical conjugates which comprise oligopeptides, having amino acid sequences that are selectively proteolytically cleaved by free prostate specific antigen (PSA), and a cytotoxic agent are disclosed. The conjugates of the invention are characterized by a diamine linker between the oligopeptide and vinblastine. Such conjugates are useful in the treatment of prostatic cancer and benign prostatic hyperplasia (BPH).

DETAILED DESCRIPTION OF THE INVENTION

The instant invention relates to novel anti-cancer compositions useful for the treatment of prostate cancer. Such compositions comprise the oligopeptides covalently bonded through a chemical linker to cytotoxic agent, preferably a vinca drug. The oligopeptides are chosen from oligomers that are selectively recognized by the free prostate specific antigen (PSA) and are capable of being proteolytically cleaved by the enzymatic activity of the free prostate specific antigen. Such a combination of an oligopeptide and cytotoxic agent may be termed a conjugate.

The conjugates of the instant invention are characterized by a linker between the C-terminus of the oligopeptide and the vinca drug. In particular, the linker is a diamine comprising a cyclic alkyl moiety and most preferably, the diamine comprises a bicycloalkyl moiety. Examples of such diamine linkers include but are not limited to 1,4-bis(aminomethyl)cyclohexane, 1,4-bis(aminomethyl)cycloheptane, 1,3-bis(aminomethyl)cyclopentane, 1-amino-4-(aminomethyl)cyclohexane, 1,4-diaminocyclohexane, 1,4-bis(aminomethyl)bicyclo[2.2.2]octane.

Ideally, the cytotoxic activity of vinblastine is greatly reduced or absent when the oligopeptide containing the PSA proteolytic cleavage site is bonded through a chemical linker to the cytotoxic agent and is intact. Also ideally, the cytotoxic activity of the cytotoxic agent increases significantly or returns to the activity of the unmodified cytotoxic agent upon proteolytic cleavage of the attached oligopeptide at the cleavage site.

Furthermore, it is preferred that the oligopeptide is selected from oligopeptides that are not cleaved or are cleaved at a much slower rate in the presence of non-PSA proteolytic enzymes, such as those enzymes endogenous to human serum, when compared to the cleavage of the oligopeptides in the presence of free enzymatically active PSA.

For the reasons above, it is desireable for the oligopeptide to comprise a short peptide sequence, preferably less than ten amino acids. Most preferably the oligopeptide comprises seven or six amino acids. Because the conjugate preferably comprises a short amino acid sequence, the solubility of the conjugate may be influenced to a greater extent by the generally hydrophobic character of the cytotoxic agent component. Therefore, amino acids with hydrophilic substituents may be incorporated in the oligopeptide sequence or N-terminus blocking groups may be selected to offset or diminish such a hydrophobic contribution by the cytotoxic agent.

While it is not necessary for practicing this aspect of the invention, a preferred embodiment of this invention is a conjugate wherein the oligopeptide and the chemical linker are detached from the cytotoxic agent by the proteolytic activity of the free PSA and any other native proteolytic enzymes present in the tissue proximity, thereby presenting the cytotoxic agent, or a cytotoxic agent that retains part of the oligopeptide/linker unit but remains cytotoxic, into the physiological environment at the place of proteolytic cleavage. Pharmaceutically acceptable salts of the conjugates are also included.

It is understood that the oligopeptide that is conjugated to the cytotoxic agent, whether through a direct covalent bond or through a chemical linker, does not need to be the oligopeptide that has the greatest recognition by free PSA and is most readily proteolytically cleaved by free PSA. Thus, the oligopeptide that is selected for incorporation in such an anti-cancer composition will be chosen both for its selective, proteolytic cleavage by free PSA and for the cytotoxic activity of the cytotoxic agent-proteolytic residue conjugate (or, in what is felt to be an ideal situation, the unmodified cytotoxic agent) which results from such a cleavage. The term "selective" as used in connection with the proteolytic PSA cleavage means a greater rate of cleavage of an oligopeptide component of the instant invention by free PSA relative to cleavage of an oligopeptide which comprises a random sequence of amino acids. Therefore, the oligopeptide component of the instant invention is a prefered substrate of free PSA. The term "selective" also indicates that the oligopeptide is proteolytically cleaved by free PSA between two specific amino acids in the oligopeptide.

The oligopeptide components of the instant invention are selectively recognized by the free prostate specific antigen (PSA) and are capable of being proteolytically cleaved by the enzymatic activity of the free prostate specific antigen. Such oligopeptides comprise an oligomer selected from:
a) AsnLyseSerTyrGln|Ser (SEQ.ID.NO.: 1),
b) LysIleSerTyrGln|Ser (SEQ.ID.NO.: 2),
c) AsnLysIleSerTyrTyr|Ser (SEQ.ID.NO.: 3),
d) AsnLysAlaSerTyrGln|Ser (SEQ.ID.NO.: 4),
e) SerTyrGln|SerSer (SEQ.ID.NO.: 5);
f) LysTyrGln|SerSer (SEQ.ID.NO.: 6);
g) hArgTyrGln|SerSer (SEQ.ID.NO.: 7);
h) hArgChaGln|SerSer (SEQ.ID.NO.: 8);
i) TyrGln|SerSer (SEQ.ID.NO.: 9);
j) TyrGln|SerLeu (SEQ.ID.NO.: 10);
k) TyrGln|SerNle (SEQ.ID.NO.: 11);
l) ChgGln|SerLeu (SEQ.ID.NO.: 12);
m) ChgGln|SerNle (SEQ.ID.NO.: 13);
n) SerTyrGln|Ser (SEQ.ID.NO.: 14);
o) SerChgGln|Ser (SEQ.ID.NO.: 15);
p) SerTyrGln|SerVal (SEQ.ID.NO.: 16);
q) SerChgGln|SerVal (SEQ.ID.NO.: 17);
r) SerTyrGln|SerLeu (SEQ.ID.NO.: 18);
s) SerChgGln|SerLeu (SEQ.ID.NO.: 19);
t) HaaXaaSerTyrGln|Ser (SEQ.ID.NO.: 20);
u) HaaXaaLysTyrGln|Ser (SEQ.ID.NO.: 21);
v) HaaXaahArgTyrGln|Ser (SEQ.ID.NO.: 22);
w) HaaXaahArgChaGln|Ser (SEQ.ID.NO.: 23);
x) HaaTyrGln|Ser (SEQ.ID.NO.: 24);
y) HaaXaaSerChgGln|Ser (SEQ.ID.NO.: 25);
z) HaaChgGln|Ser (SEQ.ID.NO.: 26);
wherein Haa is a cyclic amino acid substituted with a hydrophilic moiety, hArg is homoarginine, Xaa is any amino acid, Cha is cyclohexylalanine and Chg is cyclohexylglycine.

In an embodiment of the instant invention, the oligopeptide comprises an oligomer that is selected from:
a) SerSerTyrGln|SerVal (SEQ.ID.NO.: 27);
b) SerSerChgGln|SerVal (SEQ.ID.NO.: 28);
c) SerSerTyrGln|SerLeu (SEQ.ID.NO.: 29);
d) SerSerChgGln|SerLeu (SEQ.ID.NO.: 30);
e) 4-HypSerSerTyrGln|Ser (SEQ.ID.NO.: 31);
f) 4-HypSerSerChgGln|Ser (SEQ.ID.NO.: 32);
h) AlaSerTyrGln|SerVal (SEQ.ID.NO.: 33);
i) AlaSerChgGln|SerVal (SEQ.ID.NO.: 34);
j) AlaSerTyrGln|SerLeu (SEQ.ID.NO.: 35);
k) AlaSerChgGln|SerLeu (SEQ.ID.NO.: 36);
l) 4-HypAlaSerTyrGln|Ser (SEQ.ID.NO.: 37);
m) 4-HypAlaSerChgGln|Ser (SEQ.ID.NO.: 38);
wherein 4-Hyp is 4-hydroxyproline, Xaa is any amino acid, hArg is homoarginine, Cha is cyclohexylalanine and Chg is cyclohexylglycine.

In a more preferred embodiment of the instant invention, the oligopeptide comprises an oligomer selected from:
SerSerChgGln|SerLeu (SEQ.ID.NO.: 39);
SerSerChgGln|SerVal (SEQ.ID.NO.: 40);
SerSerSerChgGln|SerLeu (SEQ.ID.NO.: 41);
SerSerSerChgGln|SerVal (SEQ.ID.NO.: 42);
SerAlaSerChgGln|SerLeu (SEQ.ID.NO.: 43);
SerAlaSerChgGln|SerVal (SEQ.ID.NO.: 44);
(N-methyl-Ser)SerSerChgGln|SerLeu (SEQ.ID.NO.: 45);
(N-methyl-Ser)SerSerChgGln|SerVal (SEQ.ID.NO.: 46);
4-HypSerSerTyrGln|SerVal (SEQ.ID.NO.: 47);

4-HypSerSerTyrGln|SerLeu (SEQ.ID.NO.: 48);
4-HypSerSerChgGln|SerVal (SEQ.ID.NO.: 49);
4-HypSerSerChgGln|SerLeu (SEQ.ID.NO.: 50);
4-HypAlaSerChgGln|SerVal (SEQ.ID.NO.: 51);
4-HypAlaSerChgGln|SerLeu (SEQ.ID.NO.: 52);
(3,4-DiHyp)SerSerTyrGln|SerVal (SEQ.ID.NO.: 53); and
(3,4-DiHyp)SerSerTyrGln|SerLeu (SEQ.ID.NO.: 54);
wherein 4-Hyp is 4-hydroxyproline, 3,4-DiHyp is 3,4-dihydroxyproline and Chg is cyclohexylglycine.

The phrase "oligomers that comprise an amino acid sequence" as used hereinabove, and elsewhere in the Detailed Description of the Invention, describes oligomers of from about 3 to about 100 amino acids residues which include in their amino acid sequence the specific amino acid sequence described and which are therefore proteolytically cleaved within the amino acid sequence described by free PSA. Preferably, the oligomer is from 5 to 10 amino acid residues. Thus, for example, the following oligomer:
hArgSerAlaChgGln|SerLeu (SEQ.ID.NO.: 55);
comprises the amino acid sequence:
ChgGln|SerLeu (SEQ.ID.NO.: 12);
and would therefore come within the instant invention. And the oligomer:
hArgSer4-HypChgGln|SerLeu (SEQ.ID.NO.: 56);
comprises the amino acid sequence:
4-HypChgGln|SerLeu (SEQ.ID.NO.: 57);
and would therefore come within the instant invention. It is understood that such oligomers do not include semenogelin I, semenogelin II, fibronectin and IGFBP-3.

A person of ordinary skill in the peptide chemistry art would readily appreciate that certain amino acids in a biologically active oligopeptide may be replaced by other homologous, isosteric and/or isoelectronic amino acids wherein the biological activity of the original oligopeptide has been conserved in the modified oligopeptide. Certain unnatural and modified natural amino acids may also be utilized to replace the corresponding natural amino acid in the oligopeptides of the instant invention. Thus, for example, tyrosine may be replaced by 3-iodotyrosine, 2-methyltyrosine, 3-fluorotyrosine, 3-methyltyrosine and the like. Further for example, lysine may be replaced with N'-(2-imidazolyl)lysine and the like. The following list of amino acid replacements is meant to be illustrative and is not limiting:

| Original Amino Acid | Replacement Amino Acid(s) |
| --- | --- |
| Ala | Gly |
| Arg | Lys, Ornithine |
| Asn | Gln |
| Asp | Glu |
| Glu | Asp |
| Gln | Asn |
| Gly | Ala |
| Ile | Val, Leu, Met, Nle |
| Leu | Ile, Val, Met, Nle |
| Lys | Arg, Ornithine |
| Met | Leu, Ile, Nle, Val |
| Ornithine | Lys, Arg |
| Phe | Tyr, Trp |
| Ser | Thr |
| Thr | Ser |
| Trp | Phe, Tyr |
| Tyr | Phe, Trp |
| Val | Leu, Ile, Met, Nle |

Thus, for example, the following oligopeptides may be synthesized by techniques well known to persons of ordinary skill in the art and would be expected to be proteolytically cleaved by free PSA:

AsnArgIleSerTyrGln|Ser (SEQ.ID.NO.: 58)
AsnLysValSerTyrGln|Ser (SEQ.ID.NO.: 59)
AsnLysMetSerTyrGln|SerSer (SEQ.ID.NO.: 60)
AsnLysLeuSerTyrGln|SerSer (SEQ.ID.NO.: 61)
AsnLysIleSerTyrGln|Ser (SEQ.ID.NO.: 62)
GlnLysIleSerTyrGln|SerSer (SEQ.ID.NO.: 63).
Asn4-HypIleSerTyrGln|Ser (SEQ.ID.NO.: 64)
Asn4-HypValSerTyrGln|Ser (SEQ.ID.NO.: 65)
4-HypAlaSerTyrGln|SerSer (SEQ.ID.NO.: 66)
(3,4-dihydroxyproline)AlaSerTyrGln|SerSer (SEQ.ID.NO.: 67)
3-hydroxyprolineSerChgGln|Ser (SEQ.ID.NO.: 68)
4-HypAlaSerChgGln|SerSer (SEQ.ID.NO.: 69).

The inclusion of the symbol "|" within an amino acid sequence indicates the point within that sequence where the oligopeptide is proteolytically cleaved by free PSA.

The compounds of the present invention may have asymmetric centers and occur as racemates, racemic mixtures, and as individual diastereomers, with all possible isomers, including optical isomers, being included in the present invention. Unless otherwise specified, named amino acids are understood to have the natural "L" stereoconfiguration In the present invention, the amino acids which are disclosed are identified both by conventional 3 letter and single letter abbreviations as indicated below:

| | | |
| --- | --- | --- |
| Alanine | Ala | A |
| Arginine | Arg | R |
| Asparagine | Asn | N |
| Aspartic acid | Asp | D |
| Asparagine or Aspartic acid | Asx | B |
| Cysteine | Cys | C |
| Glutamine | Gln | Q |
| Glutamic acid | Glu | E |
| Glutamine or Glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The following abbreviations are utilized in the specification and figures to denote the indicated amino acids and moieties:
hR or hArg: homoarginine
hY or hTyr: homotyrosine
Cha: cyclohexylalanine
Amf: 4-aminomethylphenylalanine
DAP: 1,3-diaminopropyl
DPL: 2-(4,6-dimethylpyrimidinyl)lysine
(imidazolyl)K: N'-(2-imidazolyl)lysine
$Me_2PO_3$-Y: O-dimethylphosphotyrosine
O-Me-Y: O-methyltyrosine
TIC: 1,2,3,4-tetrahydro-3-isoquinoline carboxylic acid
DAP: 1,3-diaminopropane
TFA: trifluoroacetic acid
AA: acetic acid
3PAL: 3-pyridylalanine
4-Hyp: 4-hydroxyproline
dAc-Vin: 4-des-acetylvinblastine It is well known in the art, and understood in the instant invention, that peptidyl therapeutic agents such as the instant oligopeptide-cytotoxic agent conjugates preferably have the terminal amino moiety of any oligopeptide substituent protected with a suitable protecting group, such as acetyl, benzoyl, pivaloyl and the like. Such protection of the terminal amino group reduces or eliminates the enzymatic degradation of such peptidyl therapeutic agents by the action of exogenous amino peptidases which are present in the blood plasma of warm blooded animals. Such protecting groups also include hydrophilic blocking groups, which are chosen based upon the presence of hydrophilic functionality. Blocking groups that increase the hydrophilicity of the conjugates and therefore increase the aqueous solubility of the conjugates include but are not limited to hydroylated alkanoyl, polyhydroxylated alkanoyl, polyethylene glycol, glycosylates, sugars and crown ethers. N-Terminus unnatural amino acid moieties may also ameleorate such enzymatic degradation by exogenous amino peptidases.

Preferably the N-terminus protecting group is selected from a) acetyl;

b)
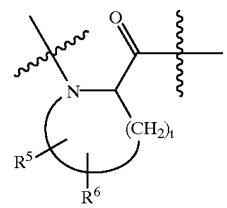

c)
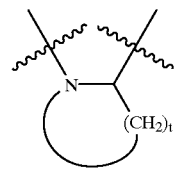

d)
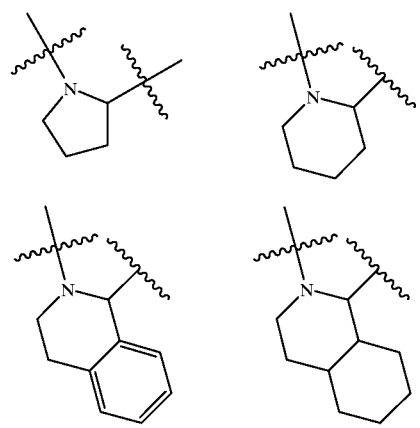

wherein:

$R^1$ and $R^2$ are independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^3O$—, $R^3C(O)NR^3$—, $(R^3)_2NC(O)$—, $R^3_2N$—$C(NR^3)$—, $R^4S(O)_2NH$, CN, $NO_2$, $R^3C(O)$—, $N_3$, —$N(R^3)_2$, or $R^4OC(O)NR^3$—,
  c) unsubstituted $C_1$–$C_6$ alkyl,
  d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^3O$—, $R^4S(O)_2NH$, $R^3C(O)NR^3$—, $(R^3)_2NC(O)$—, $R^3_2N$—$C(NR^3)$—, CN, $R^3C(O)$—, $N_3$, —$N(R^3)_2$, and $R^4OC(O)$—$NR^3$—; or $R^1$ and $R^2$ are combined to form —$(CH_2)_s$— wherein one of the carbon atoms is optionally replaced by a moiety selected from: O, $S(O)_m$, —NC(O)—, NH and —$N(COR^4)$—;

$R^3$ is selected from: hydrogen, aryl, substituted aryl, heterocycle, substituted heterocycle, $C_1$–$C_6$ alkyl and $C_3$–$C_{10}$ cycloalkyl;

$R^4$ is selected from: aryl, substituted aryl, heterocycle, substituted heterocycle, $C_1$–$C_6$ alkyl and $C_3$–$C_{10}$ cycloalkyl;

m is 0, 1 or 2;

n is 1, 2, 3 or 4;

p is zero or an integer between 1 and 100; and q is 0 or 1, provided that if p is zero, q is 1; and r is 1, 2 or 3;

s is 3, 4 or 5.

Certain of the oligopeptides of the instant conjugates comprise a cyclic amino acid substituted with a hydrophilic moiety, previously represented by the term "Haa", which may also be represented by the formula:

wherein:

$R^5$ is selected from HO— and $C_1$–$C_6$ alkoxy;

$R^6$ is selected from hydrogen, halogen, $C_1$–$C_6$ alkyl, HO— and $C_1$–$C_6$ alkoxy; and t is 3 or 4.

The structure represents a cyclic amine moiety having 5 or 6 members in the ring, such a cyclic amine which may be optionally fused to a phenyl or cyclohexyl ring. Examples of such a cyclic amine moiety include, but are not limited to, the following specific structures:

The conjugates of the present invention may have asymmetric centers and occur as racemates, racemic mixtures, and as individual diastereomers, with all possible isomers, including optical isomers, being included in the present invention. When any variable (e.g. aryl, heterocycle, $R^3$ etc.) occurs more than one time in any constituent, its definition on each occurence is independent of every other occurence.

For example, HO(CR$^1$R$^2$)$_2$— represents HOCH$_2$CH$_2$—, HOCH$_2$CH(OH)—, HOCH(CH$_3$)CH(OH)—, etc. Also, combinations of substituents and/or variables are permissible only if such combinations result in stable compounds.

As used herein, "alkyl" and the alkyl portion of aralkyl and similar terms, is intended to include both branched and straight-chain saturated aliphatic hydrocarbon groups having the specified number of carbon atoms; "alkoxy" represents an alkyl group of indicated number of carbon atoms attached through an oxygen bridge.

As used herein, "cycloalkyl" is intended to include non-aromatic cyclic hydrocarbon groups having the specified number of carbon atoms. Examples of cycloalkyl groups include cyclopropyl, cyclobutyl, cyclopentyl, cyclohexyl and the like.

"Alkenyl" groups include those groups having the specified number of carbon atoms and having one or several double bonds. Examples of alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl, isoprenyl, farnesyl, geranyl, geranylgeranyl and the like.

"Alkynyl" groups include those groups having the specified number of carbon atoms and having one triple bonds. Examples of alkynyl groups include acetylene, 2-butynyl, 2-pentynyl, 3-pentynyl and the like.

"Halogen" or "halo" as used herein means fluoro, chloro, bromo and iodo.

As used herein, "aryl," and the aryl portion of aralkyl and aroyl, is intended to mean any stable monocyclic or bicyclic carbon ring of up to 7 members in each ring, wherein at least one ring is aromatic. Examples of such aryl elements include phenyl, naphthyl, tetrahydronaphthyl, indanyl, biphenyl, phenanthryl, anthryl or acenaphthyl.

The term heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl.

As used herein in the terms "substituted C$_{1-8}$ alkyl", "substituted aryl" and "substituted heterocycle" include moieties containing from 1 to 3 substituents in addition to the point of attachment to the rest of the compound. Such additional substituents are selected from F, Cl, Br, CF$_3$, NH$_2$, N(C$_1$–C$_6$ alkyl)$_2$, NO$_2$, CN, (C$_1$–C$_6$ alkyl)O—, —OH, (C$_1$–C$_6$ alkyl)S(O)$_m$—, (C$_1$–C$_6$ alkyl)C(O)NH—, H$_2$N—C (NH)—, (C$_1$–C$_6$ alkyl)C(O)—, (C$_1$–C$_6$ alkyl)OC(O)—, N$_3$, (C$_1$–C$_6$ alkyl)OC(O)NH— and C$_1$–C$_{20}$ alkyl.

When R$^1$ and R$^2$ are combined to form —(CH$_2$)$_s$—, the cyclic moieties and heteroatom-containing cyclic moieties so defined include, but are not limited to:

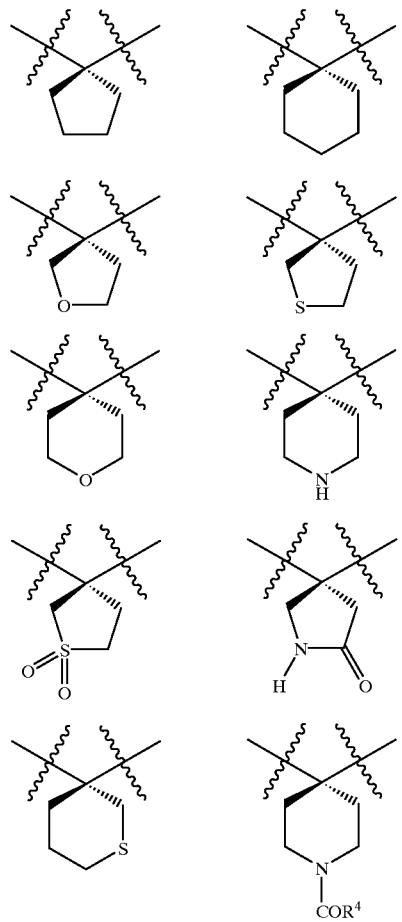

As used herein, the term "hydroxylated" represents substitution on a substitutable carbon of the ring system being so described by a hydroxyl moiety. As used herein, the term "polyhydroxylated" represents substitution on two or more substitutable carbon of the ring system being so described by 2, 3 or 4 hydroxyl moieties.

As used herein, the term "PEG" represents certain polyethylene glycol containing substituents having the designated number of ethyleneoxy subunits. Thus the term PEG (2) represents

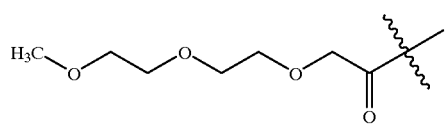

and the term PEG(6) represents

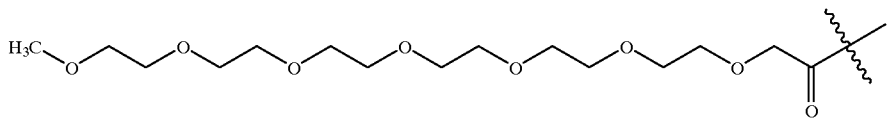

As used herein, the term "(d)(2,3-dihydroxypionyl)" represents the following structure:

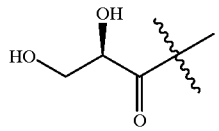

As used herein, the term "(2R,3S) 2,3,4-trihydroxybutanoyl" represents the following structure:

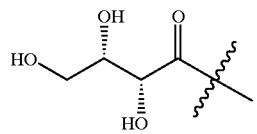

As used herein, the term "quinyl" represents the following structure:

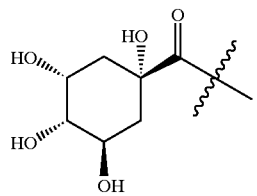

or the diastereomer thereof.

As used herein, the term "gulonic" represents the following structure:

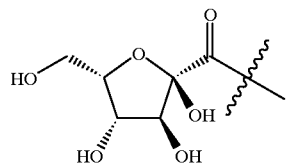

or the diastereomer thereof.

As used herein, the term "cotininyl" represents the following structure:

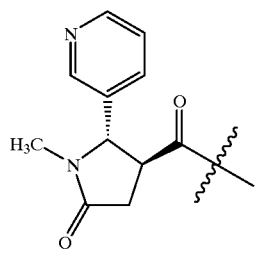

or the diastereomer thereof.

As used herein, the term "gallyl" represents the following structure:

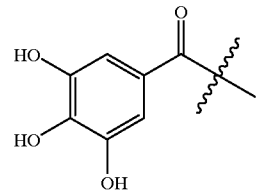

As used herein, the term "4-ethoxysquarate" represents the following structure:

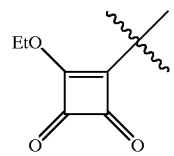

As used herein, the terms "BDAM" and "1,4-BDAM" both represent bis-1,4-aminomethylbicyclo-[2.2.2]octane:

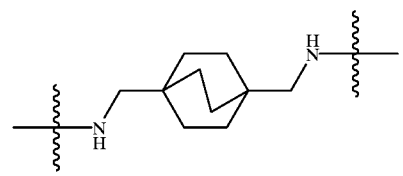

The cytotoxic agent that is utilized in the conjugates of the instant invention may be selected from alkylating agents, anti-proliferative agents, tubulin binding agents and the like. Preferred classes of cytotoxic agents which may be linked to cleavable oligomers via the diamino linker include, for example, the methotrexates, the vinca drugs (also known as vinca alkaloid cytotoxic agents), the mitomycins and the bleomycins. Particularly useful members of those classes include, for example, aminopterin, methotrexate, methopterin, dichloro-methotrexate, mitomycin C, porfiromycin, melphalan, vinblastine, vincristine, leurosidine, vindesine, leurosine and the like. Other useful cytotoxic agents include cisplatin and cyclophosphamide. One skilled in the art may make chemical modifications to the desired cytotoxic agent in order to make reactions of that compound more convenient for purposes of preparing conjugates of the invention.

The preferred cytotoxic agents include, in general, the vinca alkaloid cytotoxic agents. Particularly useful members of this class include, for example, vinblastine, desacetylvinblastine, vincristine, leurosidine, vindesine, vinorelbine, navelbine, leurosine and the like. One skilled in the art may make chemical modifications to the desired cytotoxic agent in order to make reactions of that compound more convenient for purposes of preparing conjugates of the invention.

The preferred group of cytotoxic agents for the present invention include drugs of the following formulae:

The Vinca Alkaloid Group of Drugs of Formula (1)

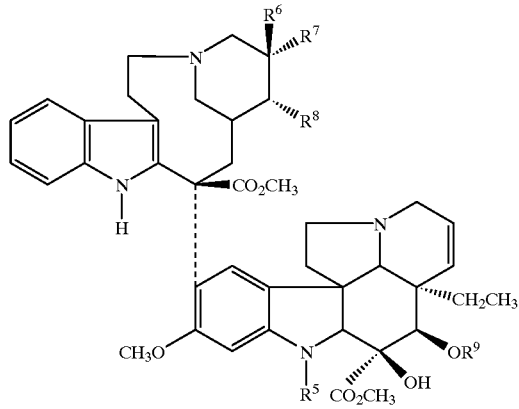

(1)

in which

R⁵ is H, CH₃ or CHO;

when $R^7$ and $R^8$ are taken singly, $R^8$ is H, and one of $R^{16}$ and $R^{17}$ is ethyl and the other is H or OH;

when $R^7$ and $R^8$ are taken together with the carbons to which they are attached, they form an oxirane ring in which case $R^6$ is ethyl;

$R^9$ is hydrogen, ($C_1$–$C_3$ alkyl)—CO, or chlorosubstituted ($C_1$–$C_3$ alkyl)—CO.

The oligopeptide-cytotoxic agent conjugate of the instant invention wherein the cytotoxic agent is the preferred cytotoxic agent vinblastine may be described by the general formula I below:

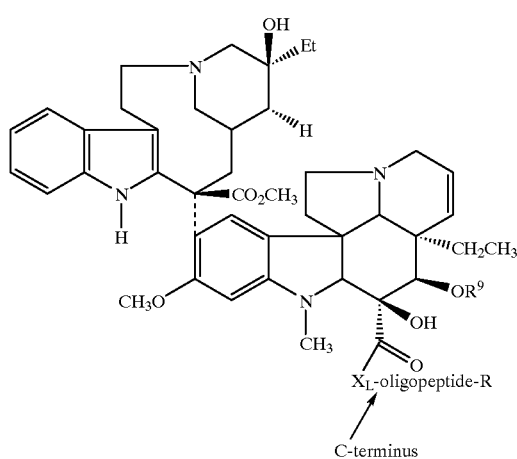

I wherein:

oligopeptide is an oligopeptide which is specifically recognized by the free prostate specific antigen (PSA) and is capable of being proteolytically cleaved by the enzymatic activity of the free prostate specific antigen, $X_L$ is —NH—$(CH_2)_u$—W—$(CH_2)_u$—NH—

R is selected from a) hydrogen,
b) 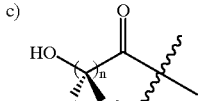—(C=O)R^{1a},
c) 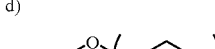

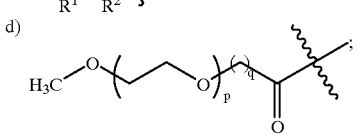

d) 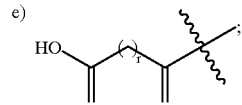

e)

f) ethoxysquarate; and
g) cotininyl;

$R^1$ and $R^2$ are independently selected from: hydrogen, OH, $C_1$–$C_6$ alkyl, $C_1$–$C_6$ alkoxy, $C_1$–$C_6$ aralkyl and aryl;

$R^{1a}$ is $C_1$–$C_6$-alkyl, hydroxylated $C_3$–$C_8$-cycloalkyl, polyhydroxylated $C_3$–$C_8$-cycloalkyl, hydroxylated aryl, polyhydroxylated aryl or aryl, $R^9$ is hydrogen, ($C_1$–$C_3$ alkyl)-CO, or chlorosubstituted ($C_1$–$C_3$ alkyl)-CO;

W is selected from cyclopentyl, cyclohexyl, cycloheptyl or bicyclo[2.2.2]octanyl;

n is 1, 2, 3 or 4;

p is zero or an integer between 1 and 100;

q is 0 or 1, provided that if p is zero, q is 1;

r is 1, 2 or 3;

t is 3 or 4;

u is 0, 1, 2 or 3, or the pharmaceutically acceptable salt thereof.

The following compounds are specific examples of the oligopeptide-desacetylvinblastine conjugate of the instant invention:

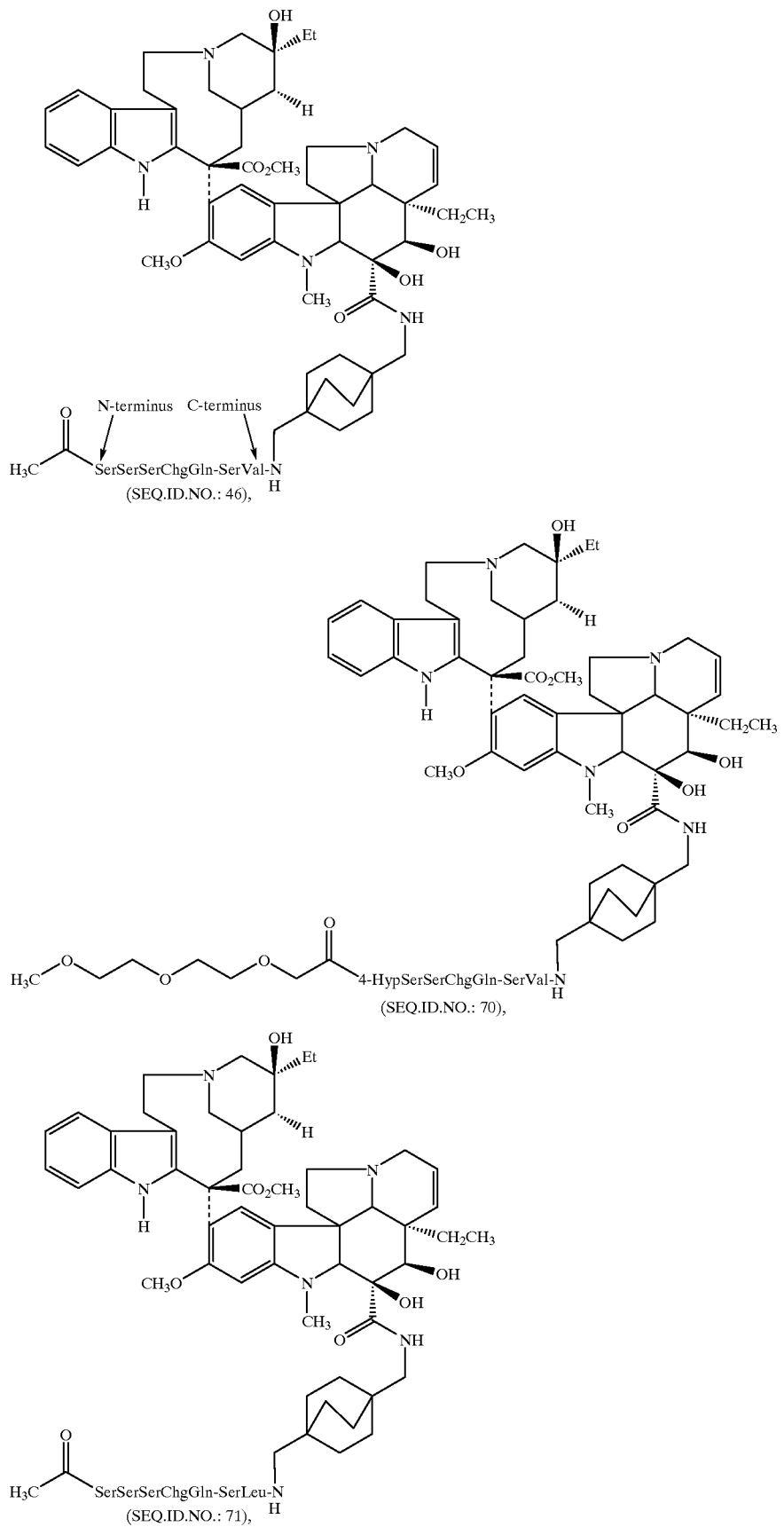

-continued

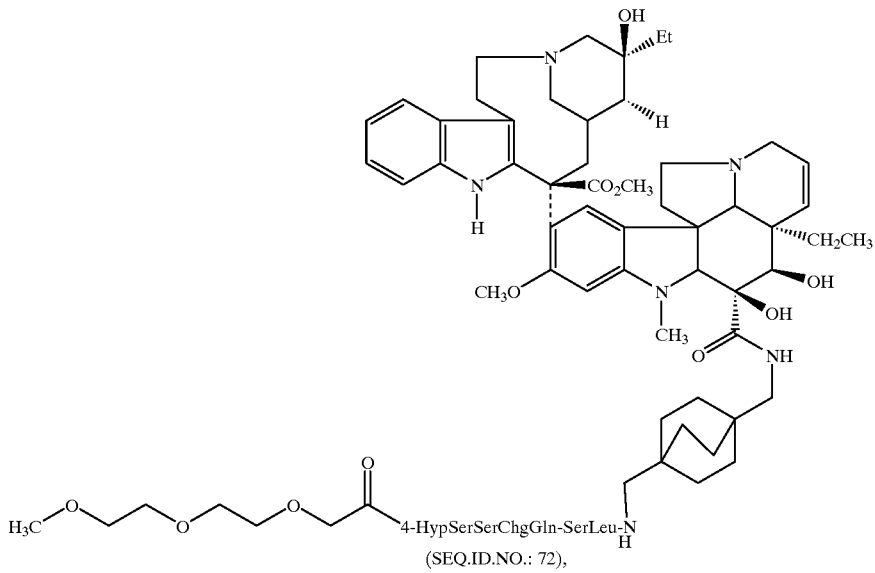

(SEQ.ID.NO.: 72), or the pharmaceutically acceptable salt thereof.

The oligopeptides, peptide subunits and peptide derivatives (also termed "peptides") of the present invention can be synthesized from their constituent amino acids by conventional peptide synthesis techniques, preferably by solid-phase technology. The peptides are then purified by reverse-phase high performance liquid chromatography (HPLC).

Standard methods of peptide synthesis are disclosed, for example, in the following works: Schroeder et al., "The Peptides", Vol. I, Academic Press 1965; Bodansky et al., "Peptide Synthesis", Interscience Publishers, 1966; McOmie (ed.) "Protective Groups in Organic Chemistry", Plenum Press, 1973; Barany et al., "The Peptides: Analysis, Synthesis, Biology" 2, Chapter 1, Academic Press, 1980, and Stewart et al., "Solid Phase Peptide Synthesis", Second Edition, Pierce Chemical Company, 1984. The teachings of these works are hereby incorporated by reference.

The suitably substituted cyclic amino acid having a hydrophilic substituent, which may be incorporated into the instant conjugates by standard peptide synthesis techniques, is itself either commercially available or is readily synthesized by techniques well known in the art or described herein. Thus syntheses of suitably substituted prolines are described in the following articles and references cited therein: J. Ezquerra et al., J. Org. Chem. 60: 2925–2930 (1995); P. Gill and W. D. Lubell, J. Org. Chem., 60:2658–2659 (1995); and M. W. Holladay et al., J. Med. Chem., 34:457–461 (1991). The teachings of these works are hereby incorporated by reference.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, trifluoroacetic and the like.

The conjugates of the instant invention which comprise the oligopeptide containing the PSA cleavage site and a cytotoxic agent may similarly be synthesized by techniques well known in the medicinal chemistry art. For example, a free amine moiety on the cytotoxic agent may be covalently attached to the oligopeptide at the carboxyl terminus such that an amide bond is formed. Similarly, an amide bond may be formed by covalently coupling an amine moiety of the oligopeptide and a carboxyl moiety of the cytotoxic agent. For these purposes a reagent such as 2-(1H-benzotriazol-1-yl)-1,3,3-tetramethyluronium hexafluorophosphate (known as HBTU) and 1-hyroxybenzotriazole hydrate (known as HOBT), dicyclohexylcarbodiimide (DCC), N-ethyl-N-(3-dimethylaminopropyl)-carbodiimide (EDC), diphenylphosphorylazide (DPPA), benzotriazol-1-yl-oxy-tris-(dimethylamino)phosphonium hexafluorophosphate (BOP) and the like, used in combination or singularly, may be utilized.

Furthermore, the instant conjugate may be formed by a non-peptidyl bond between the PSA cleavage site and a cytotoxic agent. For example, the cytotoxic agent may be covalently attached to the carboxyl terminus of the oligopeptide via a hydroxyl moiety on the cytotoxic agent, thereby forming an ester linkage. For this purpose a reagent such as a combination of HBTU and HOBT, a combination of BOP and imidazole, a combination of DCC and DMAP, and the like may be utilized. The carboxylic acid may also be activated by forming the nitrophenyl ester or the like and reacted in the presence of DBU (1,8-diazabicyclo[5,4,0]undec-7-ene.

One skilled in the art understands that in the synthesis of compounds of the invention, one may need to protect various reactive functionalities on the starting compounds and intermediates while a desired reaction is carried out on other portions of the molecule. After the desired reactions are complete, or at any desired time, normally such protecting groups will be removed by, for example, hydrolytic or hydrogenolytic means. Such protection and deprotection steps are conventional in organic chemistry. One skilled in the art is referred to Protective Groups in Organic Chemistry, McOmie, ed., Plenum Press, NY, N.Y. (1973); and, Protective Groups in Organic Synthesis, Greene, ed., John Wiley & Sons, NY, N.Y. (1981) for the teaching of protective groups which may be useful in the preparation of compounds of the present invention.

By way of example only, useful amino-protecting groups may include, for example, $C_1$–$C_{10}$ alkanoyl groups such as formyl, acetyl, dichloroacetyl, propionyl, hexanoyl, 3,3-diethylhexanoyl, γ-chlorobutryl, and the like; $C_1$–$C_{10}$ alkoxycarbonyl and $C_5$–$C_{15}$ aryloxycarbonyl groups such as tert-butoxycarbonyl, benzyloxycarbonyl, allyloxycarbonyl, 4-nitrobenzyloxycarbonyl, fluorenylmethyloxycarbonyl and cinnamoyloxycarbonyl; halo-($C_1$–$C_{10}$)-alkoxycarbonyl such as 2,2,2-trichloroethoxycarbonyl; and $C_1$–$C_{15}$ arylalkyl and alkenyl group such as benzyl, phenethyl, allyl, trityl, and the like. Other commonly used amino-protecting groups are those in the form of enamines prepared with β-keto-esters such as methyl or ethyl acetoacetate.

Useful carboxy-protecting groups may include, for example, $C_1$–$C_{10}$ alkyl groups such as methyl, tert-butyl, decyl; halo-$C_1$–$C_{10}$ alkyl such as 2,2,2-trichloroethyl, and 2-iodoethyl; $C_5$–$C_{15}$ arylalkyl such as benzyl, 4-methoxybenzyl, 4-nitrobenzyl, triphenylmethyl, diphenylmethyl; $C_1$–$C_{10}$ alkanoyloxymethyl such as acetoxymethyl, propionoxymethyl and the like; and groups such as phenacyl, 4-halophenacyl, allyl, dimethylallyl, tri-($C_1$–$C_3$ alkyl) silyl, such as trimethylsilyl, β-p-toluenesulfonylethyl, β-p-nitrophenylthioethyl, 2,4,6-trimethylbenzyl, β-methylthioethyl, phthalimidomethyl, 2,4-dinitrophenylsulphenyl, 2-nitrobenzhydryl and related groups.

Similarly, useful hydroxy protecting groups may include, for example, the formyl group, the chloroacetyl group, the benzyl group, the benzhydryl group, the trityl group, the 4-nitrobenzyl group, the trimethylsilyl group, the phenacyl group, the tert-butyl group, the methoxymethyl group, the tetrahydropyranyl group, and the like.

With respect to the preferred embodiment of an oligopeptide combined with vinblastine or desacetylvinblastine, the following Reaction Schemes illustrate the synthsis of the conjugates of the instant invention.

Reaction Scheme I illustrates preparation of conjugates of the oligopeptides of the instant invention and the vinca alkaloid cytotoxic agent vinblastine wherein the attachment of vinblastine is at the C-terminus of the oligopeptide. Furthermore, Scheme I illustrates a synthesis of conjugates wherein the C-4-position hydroxy moiety is reacetylated following the addition of the linker unit. Applicants have discovered that the desacetyl vinblastine conjugate is also efficacious and may be prepared by eliminating the steps shown in Reaction Scheme I of protecting the primary amine of the linker and reacting the intermediate with acetic anhydride, followed by deprotection of the amine. Conjugation of the oligopeptide at other positions and functional groups of vinblastine may be readily accomplished by one of ordinary skill in the art and is also expected to provide compounds useful in the treatment of prostate cancer.

REACTION SCHEME I

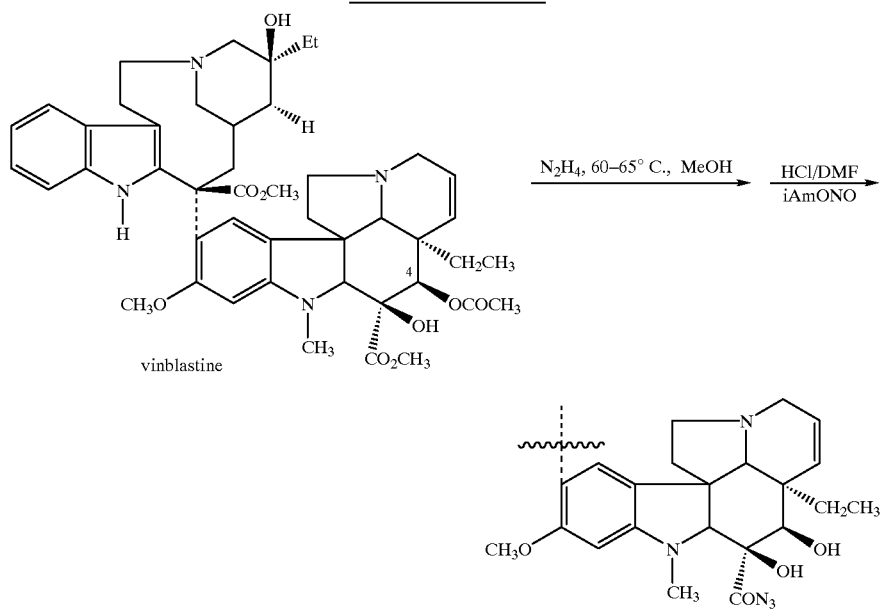

-continued

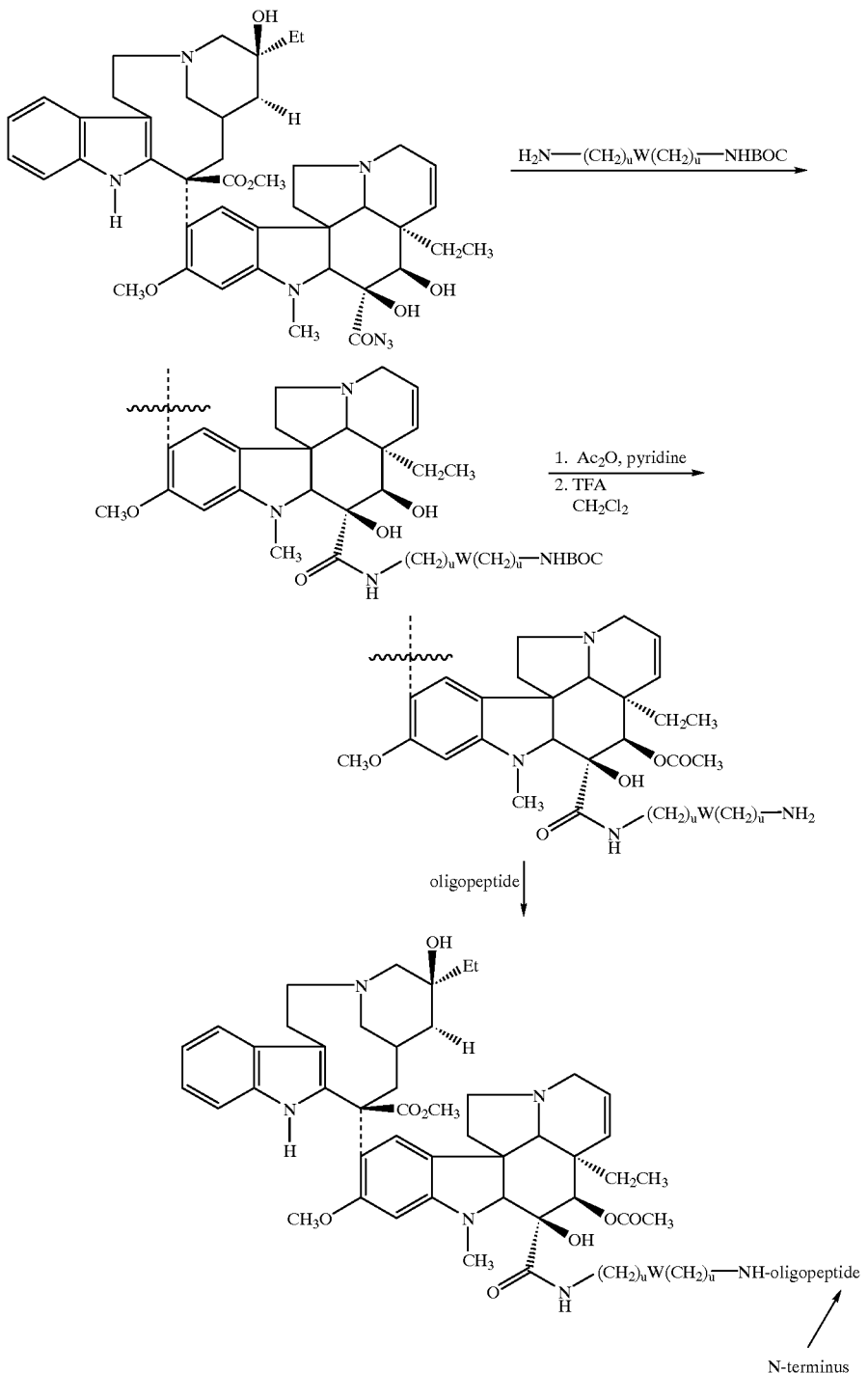

The oligopeptide-cytotoxic agent conjugates of the invention are administered to the patient in the form of a pharmaceutical composition which comprises a conjugate of of the instant invention and a pharmaceutically acceptable carrier, excipient or diluent therefor. As used, "pharmaceutically acceptable" refers to those agents which are useful in the treatment or diagnosis of a warm-blooded animal including, for example, a human, equine, procine, bovine, murine, canine, feline, or other mammal, as well as an avian or other warm-blooded animal. The preferred mode of administration is parenterally, particularly by the intravenous, intramuscular, subcutaneous, intraperitoneal, or intralymphatic route. Such formulations can be prepared using carriers, diluents or excipients familiar to one skilled in the art. In this regard, See, e.g. *Remington's Pharmaceutical Sciences,* 16th ed., 1980, Mack Publishing Company, edited by Osol et al. Such compositions may include proteins, such as serum proteins, for example, human serum albumin, buffers or buffering substances such as phosphates, other salts, or electrolytes, and the like. Suitable diluents may include, for example, sterile water, isotonic saline, dilute aqueous dextrose, a polyhydric alcohol or mixtures of such alcohols, for example, glycerin, propylene glycol, polyethylene glycol and the like. The compositions may contain preservatives such as phenethyl alcohol, methyl and propyl parabens, thimerosal, and the like. If desired, the composition can include about 0.05 to about 0.20 percent by weight of an antioxidant such as sodium metabisulfite or sodium bisulfite.

As used herein, the term "composition" is intended to encompass a product comprising the specified ingredients in the specific amounts, as well as any product which results, directly or indirectly, from combination of the specific ingredients in the specified amounts.

For intravenous administration, the composition preferably will be prepared so that the amount administered to the patient will be from about 0.01 to about 1 g of the conjugate. Preferably, the amount administered will be in the range of about 0.2 g to about 1 g of the conjugate. The conjugates of the invention are effective over a wide dosage range depending on factors such as the disease state to be treated or the biological effect to be modified, the manner in which the conjugate is administered, the age, weight and condition of the patient as well as other factors to be determined by the treating physician. Thus, the amount administered to any given patient must be determined on an individual basis.

One skilled in the art will appreciate that although specific reagents and reaction conditions are outlined in the following examples, modification can be made which are meant to be encompassed by the spirit and scope of the invention. The following preparations and examples, therefore, are provided to further illustrate the invention, and are not limiting.

EXAMPLES

Example 1

Preparation of 4-des-Acetylvinblastine-23-(4'-aminomethylbicyclo[2.2.2]octane) methylamide (BDAM-(dAc)vinblastine)

Step A Preparation of 4-des-Acetylvinblastine-23-hydrazide

A sample of 3.99 g (4.38 mmol) of vinblastine sulfate (Sigma V-1377) was dissolved in 30.4 ml of 1:1 (v/v) absolute ethanol/anhydrous hydrazine, under $N_2$, and the solution was heated in an oil bath at 60–65° C. for 23 hr. Upon cooling, the solution was evaporated to a thick paste, which was partitioned between 300 ml of $CH_2Cl_2$ and 150 ml of saturated $NaHCO_3$. The aqueous layer was washed with 2 100-ml portions of $CH_2Cl_2$, and each of the 3 $CH_2Cl_2$ layers in turn was washed with 100 ml each of H2O (2×) and saturated NaCl (1×). The combined organic layers were dried over anhydrous $Na_2SO_4$, and the solvent was removed in vacuo to yield, after drying 20 hr in vacuo, the title compound as a white crystalline solid. This material was dissolved in 82 ml of dry, degassed DMF for storage at −20° C. until use (conc. 36 mg/ml).

Step B Boc-4-aminomethylbicyclo-[2.2.2]octane carboxylic acid

A sample of 8.79 g (40.0 mmol) of 4-carboxybicyclo [2.2.2]octanemethylamine hydrochloride salt suspended in 100 ml each of THF and $H_2O$ was treated with 20.0 ml (14.6 g=3.3 equiv.) of TEA, followed by 11.8 g (47.9 mmol) of BOC-ON reagent. All went into solution, and after stirring 24 hr the solution was concentrated in vacuo to a volume of about 50 ml and partitioned between 100 ml of ether and 300 ml of $H_2O$. After addition of about 2 ml of TEA the aqueous layer was washed with ether (3×), each ether in turn washed with $H_2O$, and the combined aqueous layer was acidified with 5% $KHSO_4$ to give the title compound as a white solid, isolated by filtration and drying in vacuo.

Step C Boc-4-aminomethylbicyclo-[2.2.2]octane carboxamide

A stirred solution under $N_2$ of 12.0 g (42.5 mmol) of the product from step B in 100 ml of DMF was treated with 8.0 g (49.3 mmol) of carbonyldiimidazole. After 30 min the DMF was evaporated in vacuo to afford 50–60 ml of a light brown paste, which was stirred and treated with 70 ml of conc. $NH_4OH$ rapidly added. The initial solution turned to a white paste within 30 min, after which $H_2O$ was added up to a total volume of 400 ml to complete precipitation of product, which was triturated and isolated by filtration and washing with $H_2O$, and dried in vacuo to yield the title compound as a white solid.

Step D Boc-4-aminomethylbicyclo-[2.2.2]octane nitrile

A solution of 7.52 g (26.6 mmol) of the product from step C in 50 ml of $CH_2Cl_2$ and 80 ml of anhydrous pyridine was treated with 11.12 g of (methoxycarbonylsulfamoyl)-triethylammonium hydroxide inner salt (Burgess reagent) in 1-g portions over 5 min. After stirring for 1.5 hr, TLC (90-10-1, $CHCl_3$-$CH_3OH$-$H_2O$) showed complete conversion to product, and the solution was evaporated to give a paste, to which $H_2O$ was added, up to 400 ml, with trituration and stirring to afford, after standing 20 hr at 0° C., filtration and drying in vacuo, the title compound as a white solid.

Step E Boc-4-aminomethylbicyclo-[2.2.2]octane methylamine

A solution of 6.75 g (25.5 mmol) of the product from step D in 200 ml of $CH_3OH$ plus 4 ml of HOAc and 2 ml of $H_2O$ was hydrogenated over 1.63 g of $PtO_2$ in a Parr shaker at 55 psi for 22 hr. The catalyst was removed by filtration through Celite, and the filtrate was concentrated in vacuo to an oily residue, which was flushed/evaporated with $CH_3OH$ (1×) and $CH_2Cl_2$ (2×). Product began to crystallize toward the end of the evaporation, and ether (up to 300 ml) was added to complete the precipitation. The white solid was triturated and isolated by filtration and washing with ether to give, after drying in vacuo, the title compound as the acetate salt.

400 Mhz 1H-NMR ($CDCl_3$): δ (ppm, TMS) 4.5 (is, Boc-NH); 2.9 (2br d, —CH2—NH—Boc); 2.45 (2br s, —CH2—NH2); 2.03 (3s, CH3COOH); 1.45 (9s, Boc); 1.40 (12s, ring CH2).

Step F Preparation of 4-des-Acetylvinblastine-23-(4'-aminomethylbicyclo-[2.2.2]octane) methylamide (BDAM-(dAc)vinblastine)

A 30-ml aliquot of the above DMF solution of 4-des-acetylvinblastine-23-hydrazide (1.41 mmol), cooled to −15° C. under Argon, was converted to the azide in situ by acidification with 4M HCl in dioxane to pH<1.5 (moistened 0–2.5 range paper), followed by addition of 0.27 ml (1.3 equiv) of isoamyl nitrite and stirring for 1 hr at 10–15° C. The pH was brought to 7 by the addition of DIEA, and a slurry of 1.27 g (3.8 mmol) of the Boc diamine product from step D above in 20 ml of DMF was then added, and the reaction was allowed to warm slowly to 15–20° C. over 2 hr, at which point coupling was complete, as monitored by analytical HPLC (A=0.1% TFA/$H_2O$; B=0.1% TFA/$CH_3CN$). The solvent was removed in vacuo and the residue partitioned between EtOAc and 5% $NaHCO_3$, the organic layer washed with 5% NaCl, and the aqueous layers back-extracted with $CH_2Cl_2$ to assure removal of the intermediary Boc-BDAM-(dAc)vinblastine. The combined organic layers were dried over $Na_2SO_4$, the solvent was removed under reduced pressure, and the residue, after flush/evaporation twice from $CH_2Cl_2$, was dissolved in 30 ml of $CH_2Cl_2$ and treated with 30 ml of TFA for 30 min. The solvents were rapidly removed in vacuo, and the residue was dissolved in 300 ml of 10% HOAc for purification by preparative HPLC in 5 portions on a Waters C4 Delta-Pak column 15 μM 300A (A=0.1% TFA/H$_2$O; B=0.1% TFA/CH$_3$CN), gradient elution 95 - - >70% A/60 min, isocratic 70%/20 min. Homogeneous fractions (evaluated by HPLC, system A, 95 - - >50% A) from the five runs were pooled and concentrated in vacuo, followed by freeze-drying to give of the title compound as the lyophilized TFA salt.

HPLC conditions, system A:
  Column      Vydac 15 cm #218TP5415, C18
  Eluant      Gradient (A → B) over 45 min.
              A = 0.1% TFA/H$_2$O, B = 0.1%
TFA/acetonitrile
  Flow        1.5 ml/min.
Retention time: BDAM (dAc) vinblastine 23.5 min.
(95% → 50% A)
                                         97% purity
High Resolution ES/FT-MS: 905.63
Compound content by elemental analysis = 0.714 μmol/mg:
  N (calc) = 9.28    N (found) = 6.00

Example 2

Preparation of 4-des-Acetylvinblastine-23-(N-Acetyl-Ser-Ser-Ser-Chg-Gln-Ser-Val-BDAM) amide acetate salt (SEQ.ID.NO.: 36)

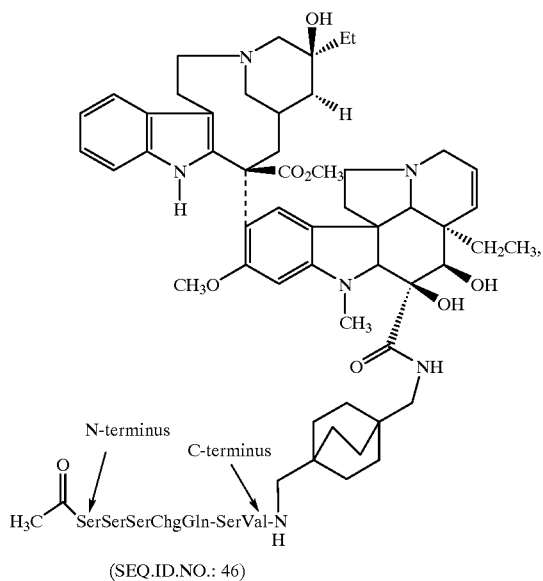

(SEQ.ID.NO.: 46)

Step A: N-Acetyl-Ser-Ser-Ser-Chg-Gln-Ser-Val-PAM Resin (SEQ.ID.NO.: 46)

Starting with 0.5 mmole (0.68 g) of Boc-Val-PAM resin, the protected peptide was synthesized on a ABI model 430A peptide synthesizer. The protocol used a 4-fold excess (2.0 mmol) of each of the following protected amino acids: Boc-Ser(Bzl)-OH, Boc-Gln-OH, Boc-Chg-OH; and acetic acid (2 couplings). During each coupling cycle Boc protection was removed using TFA, followed by neutralization with DIEA. Coupling was achieved using DCC and HOBt activation in N-methyl-2-pyrrolidinone. At the completion of the synthesis, the peptide resin was dried to yield the title compound.

Step B: N-Acetyl-Ser-Ser-Ser-Chg-Gln-Ser-Val-OH (SEQ.ID.NO.: 46)

Three 0.5-mmol runs of the above peptide-resin (3.5 g) were combined and treated with liquid HF (65 ml) for 1.5 hr at 0° C. in the presence of anisole (6 ml). After evaporation of the HF, the residue was washed with ether, filtered and leached with 150 ml of DMF in several portions, adding DIEA to pH ~8, followed by removal of the DMF in vacuo to a volume of 100 ml. The concentration was determined as ca. 11.7 mg/ml (by weighing the dried resin before and after leaching. The sample purity was determined as 96% by HPLC. The solution was used directly for conjugation with BDAM-(dAc)vinblastine.

Step C: 4-Des-acetylvinblastine-23-(N-Acetyl-Ser-Ser-Ser-Chg-Gln-Ser-Val-BDAM) amide acetate salt To 58 ml (equivalent to 0.875 mmol of peptide) of the solution from step B was added 530 mg (0.520 mmol) of BDAM-(dAc)vinblastine, prepared as above, under N2, cooling to 0° C., and the pH was adjusted to ~8 (moistened 5–10 range pH paper) with DIEA. Then 0.134 ml (0.62 mmol) of DPPA was added, followed by stirring at 0–5° C. until completion of the coupling as monitored by analytical HPLC (A=0.1% TFA/H$_2$O; B=0.1% TFA/CH$_3$CN), maintaining the pH at ≧7 by periodic addition of DIEA. After 24 hr the reaction was worked up by addition of 10 ml of H$_2$O, stirring 1 hr and concentration to small volume in vacuo, then dissolution in ca. 100 ml of 10% HOAc/5% CH$_3$CN, adjustment of the pH to 5 with NH$_4$HCO$_3$, filtration to remove insolubles, and preparative HPLC in 3 portions on a Waters C4 Delta-Pak column 15 μM 300A (A=0.1% NH$_4$HCO$_3$/H$_2$O; B=CH$_3$CN), gradient elution 95 - - >40% A/70 min. Fractions from each run containing product were pooled, acidified to pH 3 with glacial HOAc, concentrated in vacuo to a volume of ~50 ml, and purified by preparative HPLC on a Waters C18 Delta-Pak column 15 μM 300A (A=0.1% TFA/H$_2$O; B=0.1% TFA/CH3CN), gradient elution 95 - - >70% A/60 min, isocratic 70%/20 min. Homogeneous fractions (evaluated by HPLC, system A, 95 - - >50% A) from all three runs were pooled and concentrated to a volume of ~100 ml., diluted with 5% CH$_3$CN, and passed through AG4X4 ion exchange resin (acetate cycle), followed by freeze-drying to give the title compound as a lyophilized powder.

HPLC conditions, system A:
  Column      Vydac 15 cm #218TP5415, C18
  Eluant      Gradient (A → B) over 45 min.
              A = 0.1% TFA/H2O, B = 0.1%
TFA/acetonitrile
  Flow        1.5 ml/min.
Retention times: BDAM (dAc) vinblastine 23.5 min.
N-Acetyl-Ser-Ser-Ser-Chg-Gln-Ser-Val-OH 14.5 min.
4-Des-acetylvinblastine-23-(N-Acetyl-Ser-Ser-Ser-Chg-
  Gln-Ser-Val-BDAM) amide 29.5 min.
High Resolution ES/FT-MS: 1662.03
Amino Acid Compositional Analysis[1] (theory/found):
  [2]Ser4/3.6    [3]Glu 1/2.10    [4]Val 1/0.7    Chg 1/0.95
  Peptide content 0.504 μmol/mg Note:
[1]20 hr, 100° C., 6N HCl
[2]Uncorrected
[3]Gln converted to Glu
[4]Incomplete hydrolysis

Example 3

Preparation of 4-des-Acetylvinblastine-23-(N-methoxy-diethyleneoxyacetyl-4-trans-L-Hyp-Ser-Ser-Chg-Gln-Ser-Val-BDAM) amide acetate salt (SEQ.ID.NO.: 70)

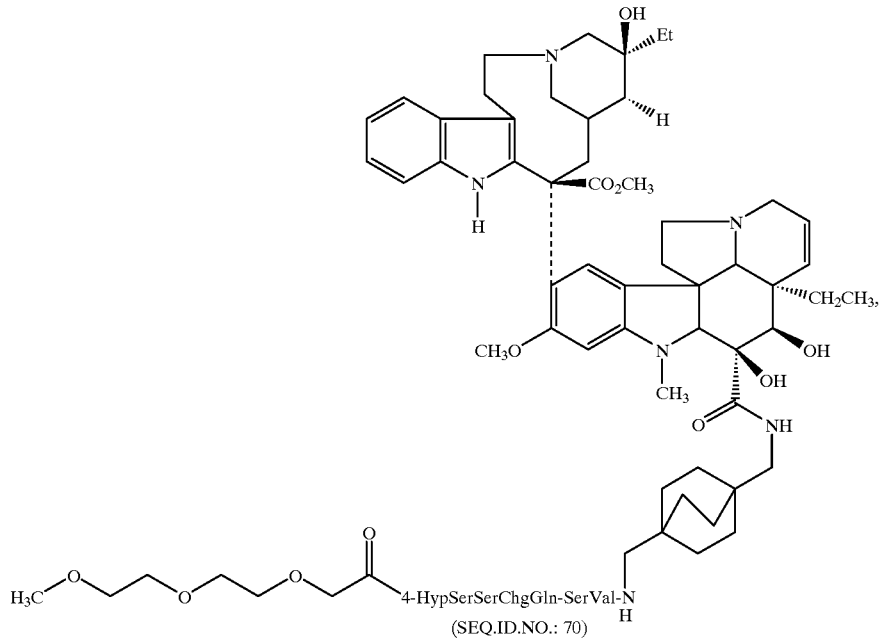
(SEQ.ID.NO.: 70)

Step A: N-methoxydiethyleneoxyacetyl-4-trans-L-Hyp-Ser-Ser-Chg-Gln-Ser-Val-PAM Resin (SEQ.ID NO.: 70)

Starting with 0.5 mmole (0.68 g) of Boc-Val-PAM resin, the protected peptide was synthesized on a ABI model 430A peptide synthesizer. The protocol used a 4-fold excess (2.0 mmol) of each of the following protected amino acids: Boc-Ser(Bzl)-OH, Boc-Gln-OH, Boc-Chg-OH, Boc-4-trans-Hyp(Bzl)-OH; and 2-[2-(2-methoxyethoxy)-ethoxy] acetic acid (2 couplings). During each coupling cycle Boc protection was removed using TFA, followed by neutralization with DIEA. Coupling was achieved using DCC and HOBt activation in N-methyl-2-pyrrolidinone. At the completion of the synthesis, the peptide resin was dried to yield the title compound.

Step B: N-methoxydiethyleneoxyacetyl-4-trans-L-Hyp-Ser-Ser-Chg-Gln-Ser-Val-OH (SEQ.ID.NO.: 70)

Two 0.5-mmol runs of the above peptide-resin (2.4 g) were combined and treated with liquid HF (40 ml) for 1.5 hr at 0° C. in the presence of anisole (4 ml). After evaporation of the HF, the residue was washed with ether, filtered and leached with 150 ml of $H_2O$ in several portions, followed by preparative HPLC on a Waters C18 Delta-Pak column 15 $\mu$M 100A (A=0.1% TFA/$H_2O$; B=0.1% TFA/$CH_3CN$), gradient elution 95 - - >70% A/70 min, and pooling of homogeneous fractions and freeze drying to give the title compound as lyophilized powder. The sample purity was determined as 99% by HPLC.

Step C: 4-des-Acetylvinblastine-23-(N-methoxydiethyleneoxyacetyl-4-trans-L-Hyp-Ser-Ser-Chg-Gln-Ser-Val-BDAM) amide acetate salt Samples of 440 mg (0.47 mmol) of the peptide from step B and 340 mg (0.33 mmol) of BDAM-(dAc)vinblastine, prepared as above, were dissolved in 25 ml of DMF under $N_2$, cooling to 0° C. Then 85 mg (0.63 mmol) of 1-hydroxy-7-azabenzotriazole (HOAt) was added, and the pH was adjusted to 6.5–7 (moistened 5–10 range pH paper) with 2,4,6-collidine, followed by addition of 117 mg (0.61 mmol) of 1-(3-dimethylaminopropyl)-3-ethylcarbodiimide hydrochloride (EDC). Stirring was continued at 0–5° C. until completion of the coupling as monitored by analytical HPLC (A=0.1% TFA/$H_2O$; B=0.1% TFA/$CH_3CN$), maintaining the pH at 6.5–7 by periodic addition of 2,4,6-collidine. After 3 hr the reaction was worked up by addition of ~10 ml of $H_2O$, stirring 1 hr and concentration to small volume in vacuo, then dissolution in ca. 70 ml of 5% HOAc. and preparative HPLC on a Waters C18 Delta-Pak column 15 $\mu$M 300A (A=0.1% TFA/$H_2O$; B=0.1% TFA/$CH_3CN$), gradient elution 95 - - >40% A/70 min). Homogeneous fractions (evaluated by HPLC, system A, 95 - - >50% A) from all three runs were pooled and concentrated to a volume of ~50 ml and passed through AG4X4 ion exchange resin (acetate cycle), followed by freeze-drying to give the title compound as a lyophilized powder.

HPLC conditions, system A:
    Column    Vydac 15 cm #218TP5415, C18
    Eluant    Gradient (A → B) over 45 min.
                  A = 0.1% TFA/$H_2O$, B = 0.1%
TFA/acetonitrile
    Flow    1.5 ml/min.
Retention times: BDAM (dAc) vinblastic 23.5 min.
M-methoxydiethyleneoxyacetyl-4-trans-L-Hyp-Ser-Ser-Chg-Gln-Ser-Val-OH  16.2 min.
4-des-Acetylvinblastine-23-(N-methoxydiethyleneoxyacetyl-4-trans-L-Hyp-Ser-Ser-Chg-Gln-Ser-Val-BDAM) amide 29.6 min.
High Resolution ES/FT-MS: 1805.95

-continued

Amino Acid Compositional Analysis[1] (theory/found):
[2]Ser3/1.7   [3]Glu 1/1.01   [4]Val 1/0.93   Chg 1/0.98   Hyp 1/1.01
Peptide content = 0.497 μmol/mg Note:
[1]20 hr, 100° C., 6N HCl
[2]Uncorrected
[3]Gln converted to Glu
[4]Incomplete hydrolysis Table 1 shows other peptide-vinca drug conjugates that were prepared by the procedures described in Examples 2 and 3, but utilizing the appropriate amino acid residues and blocking group acylation. Unless otherwise indicated, the acetate salt of the conjugate was prepared and tested.

TABLE 1

| SEQ. ID. NO. | PEPTIDE-VIN CONJUGATE | Time to 50% Substrate Cleavage by York PSA (Min) |
|---|---|---|
| 73 | Ac-SSSChgQ-SV-DAP(dAc)VIN | 25 |
| 74 | Ac-PSSChgQ-SV-DAP(dAc)VIN | 45 |
| 73 | Ac-SSSChgQSV-1,4-BDAM-(dAc)-VIN | 10 |
| 75 | Ac-SSSChgQ-S(dV)-1,4-BDAM-(dAc)-VIN | 80 |
| 76 | Ac-SSSChgQ-S-BDAM-(dAc)-VIN | 12 |
| 77 | (2-OH)Ac-(4-trans-L-Hyp)SSChgQ-SV-BDAM-(dAc)-VIN | 15 |
| 78 | PEG(2)-(4-trans-L-Hyp)-SSChgQSV-BDAM-(dAc)-VIN | 14 (n = 2) |
| 79 | PEG(2)-3,4-(diOH)P-SSChgQ-SV-BDAM-(dAc)-VIN | 17 |
| 80 | Ac-3,4-(diOH)PSSChgQ-SV-BDAM-(dAc)-VIN | 11 |
| 81 | Succinyl-(4-trans-L-Hyp)SSChgQ-SV-BDAM-(dAc)-VIN | 30 |
| 82 | PEG(2)-(N-Me-S)SSChgQ-SV-BDAM-(dAc)-VIN | 18 |
| 83 | (N-Me-S)SSChgQ-SV-BDAM-(dAc)-VIN | 13 |
| 84 | Quinyl-SSSChgQ-SV-BDAM-(dAc)-VIN | 17 (n = 2) |
| 84 | Quinyl-SSSChgQSV-BDAM-(dAc)-VIN (sulfate salt) | 25 |
| 85 | Gallyl-SSSChgQ-SV-BDAM-(dAc)-VIN | 60 |
| 103 | Ac-keto-(4-trans-L-Hyp)SSChgQ-SV-BDAM-(dAc)-VIN | 10 |
| 86 | PEG(2)-(4-trans-L-Hyp)ASChgQ-SV-BDAM-(dAc)-VIN | 14 |
| 88 | Ac-HASChgQ-SV-BDAM-(dAc)-VIN | 8 |
| 87 | 4-imidazoleacetyl-(4-trans-L-Hyp)SSChgQSV-BDAM-(dAc)-VIN | 5 |
| 87 | 4-imidazoleacetyl-(4-trans-L-Hyp)SSChgQSV-BDAM-(dAc)-VIN (sulfate salt) | 15 |
| 92 | Cotininyl-(4-trans-L-Hyp)SSChgQSV-BDAM-(dAc)-VIN | 13 |
| 92 | Cotininyl-(4-trans-L-Hyp)SSChgQSV-BDAM-(dAc)-VIN (sulfate salt) | |
| 93 | 3-phosphonylpropionyl-(4-trans-L-Hyp)SSChgQSV-BDAM-(dAc)-VIN | 40 |
| 73 | Ac-SSSChgQSV-BDAM-(dAc)-VIN (sulfate salt) | 9 |
| 89 | PEG(2)-C(SO3)-SSChgQSV-BDAM-(dAc)-VIN | 30 |
| 90 | Gulonic-(4-trans-L-Hyp)-SSChgQSV-BDAM-(dAc)-VIN | 43 |
| 91 | 4-phosphonylbutylryl-(4-trans-L-Hyp)SSChgQSV-BDAM-(dAc)-VIN | 60 |
| 94 | Succinyl-(4-trans-L-Hyp)SSChgQ-SV-BDAM-(dAc)-VIN sulfate salt | 32 |
| 95 | Glutaryl-(4-trans-L-Hyp)SSChgQ-SV-BDAM-(dAc)-VIN | 30 |
| 96 | Ethoxysquarate-(4-trans-L-Hyp)SSChg-SV-BDAM-(dAc)-VIN | 33 |
| 97 | PEG2-(4-trans-L-Hyp)SSChgQSL-BDAM-(dAc)-VIN acetate salt | 27 |
| 98 | Ac-SSSChgQSL-BDAM-(dAc)-VIN | 25 |
| 99 | Ac-HSSChgQSL-BDAM-(dAc)-VIN | PS |
| 100 | Glutaryl-(4-trans-L-Hyp)ASChgQ-SL-BDAM-(dAc)-VIN | 33 |
| 101 | Ac-SChgQ-SL-BDAM-(dAc)-VIN | PS |
| 102 | Ac-SSChgQ-SL-BDAM-(dAc)-VIN | 1 HOUR = 34% |

4-trans-L-Hyp is trans-4-hydroxy-L-proline
C(SO3) is —NHCH(CH$_2$CH$_2$SO$_3^-$)CO$_2$—
3,4-(diOH)P is

TABLE 1-continued

| SEQ. ID. NO. | PEPTIDE-VIN CONJUGATE | Time to 50% Substrate Cleavage by York PSA (Min) |
|---|---|---|

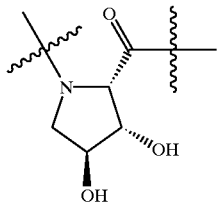

Ac-keto-(4-trans-L-Hyp) is

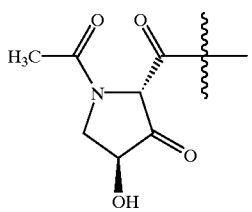

PS = partially soluble
when n > 1; value is an average

Example 4

Assessment of the Recognition of Oligopeptide-Vinca Drug Conjugates by Free PSA The conjugates prepared as described in Example 3 were individually dissolved in PSA digestion buffer (50 mM tris(hydroxymethyl)-aminomethane pH7.4, 140 mM NaCl) and the solution added to PSA at a molar ration of 100 to 1. Alternatively, the PSA digestion buffer utilized is 50 mM tris(hydroxymethyl)aminomethane pH7.4, 140 mM NaCl. The reaction is quenched after various reaction times by the addition of trifluoroacetic acid (TFA) to a final 1% (volume/volume). Alternatively the reaction is quenched with 10 mM $ZnCl_2$. The quenched reaction was analyzed by HPLC on a reversed-phase C18 column using an aqueous 0.1%TFA/acetonitrile gradient. The results of the assessment are shown in Table 1. Table 1 shows the amount of time (in minutes) required for 50% cleavage of the noted oligopeptide-cytotoxic agent conjugates with enzymatically active free PSA. Unless otherwise indicated, the acetate salt of the conjugate was tested.

Example 5

In vitro Assay of Cytotoxicity of Peptidyl Derivatives of Vinca Drugs

The cytotoxicities of the cleaveable oligopeptide-vinca drug conjugates, prepared as described in Example 3, against a line of cells which is known to be killed by unmodified vinca drug was assessed.

TABLE 2

| SEQ. ID NO. | PEPTIDE-VIN CONJUGATE | LNCaP Cell Kill in 72 HRS, {48 HRS} EC 50 ($\mu$M) |
|---|---|---|
| 87 | 4-imidazoleacetyl-(4-trans-L-Hyp)SSChgQSV-BDAM-(dAc)-VIN | PS |
| 87 | 4-imidazoleacetyl-(4-trans-L-Hyp)SSChgQSV-BDAM-(dAc)-VIN (sulfate salt) | 2.1 (C320 > 150) |
| 88 | Ac-HASChgQSV-BDAM-(dAc)-VIN | 2.4 (C320 = 100) n = 2 |
| 89 | PEG(2)-C(SO3)-SSChgQSV-BDAM-(dAc)-VIN | 1.6 (C320 > 140) |
| 80 | Gulonic-(4-trans-L-Hyp)-SSChgQSV-BDAM-(dAc)-VIN | 1.6 (C320 > 125) PS |
| 81 | 4-phosphonylbutylryl-(4-trans-L-Hyp)SSChgQSV-BDAM-(dAc)-VIN | 2.1 (C320 = 125) PS |
| 92 | Cotininyl-(4-trans-L-Hyp)SSChgQSV-BDAM-(dAc)-VIN | 1.2 (C320 > 100) |
| 92 | Cotininyl-(4-trans-L-Hyp)SSChgQSV-BDAM-(dAc)-VIN (sulfate salt) | 1.8 (C320 > 100) |
| 93 | 3-phosphonylpropionyl-(4-trans-L-Hyp)SSChgQSV-BDAM-(dAc)-VIN | 0.8 (C320 > 105) |
| 94 | Succinyl-(4-trans-L-Hyp)SSChg-SV-BDAM-(dAc)-VIN sulfate salt | 2.5 (C320 = 80) |

TABLE 2-continued

| SEQ. ID NO. | PEPTIDE-VIN CONJUGATE | LNCaP Cell Kill in 72 HRS, {48 HRS} EC 50 ($\mu$M) |
|---|---|---|
| 95 | Glutaryl-(4-trans-L-Hyp)SSChgQ-SV-BDAM-(dAc)-VIN | 2.1 (C320 > 80) |
| 96 | Ethoxysquarate-(4-trans-L-Hyp)SSChgQ-SV-BDAM-(dAc)-VIN | 1.0 (C320 > 95) |
| 97 | PEG2-(4-trans-L-Hyp)SSChgQSL-BDAM-(dAc)-VIN | 0.4 (C320 = 160) |
| 98 | Ac-SSSChgQSL-BDAM-(dAc)-VIN | 0.6 (C320 > 160) |
| 99 | Ac-HSSChgQSL-BDAM-(dAc)-VIN | 0.3 (C320 = 21) n = 2 |
| 100 | Glutaryl-(4-trans-L-Hyp)ASChgQ-SL-BDAM-(dAc)-VIN | 0.5 (C320 > 90) |

Example 6

In vivo Efficacy of Peptidyl-Cytotoxic Agent Conjugates

LNCaP.FGC or C320 cells are trypsinized, resuspended in the growth medium and centifuged for 6 mins. at 200× g. The cells are resuspended in serum-free α-MEM and counted. The appropriate volume of this solution containing the desired number of cells is then transferred to a conical centrifuge tube, centrifuged as before and resuspended in the appropriate volume of a cold 1:1 mixture of α-MEM-Matrigel. The suspension is kept on ice until the animals are inoculated.

Harlan Sprague Dawley male nude mice (10–12 weeks old) are restrained without anesthesia and are inoculated with 0.5 mL of cell suspension on the left flank by subcutaneous injection using a 22G needle. Mice are either given approximately 5×10⁵ DuPRO cells or 1.5×10⁷ LNCaP.FGC cells.

Following inoculation with the tumor cells the mice are treated under one of two protocols:

Protocol A:

One day after cell inoculation the animals are dosed with a 0.1–0.5 mL volume of test conjugate, vinca drug or vehicle control (sterile water). Dosages of the conjugate and vinca drug are initially the maximum non-lethal amount, but may be subsequently titrated lower. Identical doses are administered at 24 hour intervals for 5 days. After 10 days, blood samples are removed from the mice and the serum level of PSA is determined. Similar serum PSA levels are determined at 5–10 day intervals. At the end of 5.5 weeks the mice are sacrificed and weights of any tumors present are measured and serum PSA again determined. The animals' weights are determined at the beginning and end of the assay.

Protocol B:

Ten days after cell inoculation, blood samples are removed from the animals and serum levels of PSA are determined. Animals are then grouped according to their PSA serum levels. At 14–15 days after cell inoculation, the animals are dosed with a 0.1–0.5 mL volume of test conjugate, vinca drug or vehicle control (sterile water). Dosages of the conjugate and vinca drug are initially the maximum non-lethal amount, but may be subsequently titrated lower. Identical doses are administered at 24 hour intervals for 5 days. Serum PSA levels are determined at 5–10 day intervals. At the end of 5.5 weeks the mice are sacrificed, weights of any tumors present are measured and serum PSA again determined. The animals' weights are determined at the beginning and end of the assay.

Example 7

In vitro Determination of Proteolytic Cleavage of Conjugates by Endogenous Non-PSA Proteases Step A: Preparation of proteolytic tissue extracts All procedures are carried out at 4° C. Appropriate animals are sacrificed and the relevant tissues are isolated and stored in liquid nitrogen. The frozen tissue is pulverized using a mortar and pestle and the pulverized tissue is transfered to a Potter-Elvejeh homogenizer and 2 volumes of Buffer A (50 mM Tris containing 1.15% KCl, pH 7.5) are added. The tissue is then disrupted with 20 strokes using first a lose fitting and then a tight fitting pestle. The homogenate is centrifuged at 10,000× g in a swinging bucket rotor (HB4-5), the pellet is discarded and the re-supernatant centrifuged at 100,000× g (Ti 70). The supernatant (cytosol) is saved.

The pellet is resuspended in Buffer B (10 mM EDTA containing 1.15% KCl, pH 7.5) using the same volume used in step as used above with Buffer A. The suspension is homogenized in a dounce homogenizer and the solution centrifuged at 100,000× g. The supernatant is discarded and the pellet resuspended in Buffer C (10 mM potassium phosphate buffer containing 0.25 M sucrose, pH 7.4), using ½ the volume used above, and homogenized with a dounce homogenizer.

Protein content of the two solutions (cytosol and membrane) is determine using the Bradford assay. Assay aliquots are then removed and frozen in liquid $N_2$. The aliquots are stored at −70° C.

Step B: Proteolytic cleavage assay

For each time point, 20 microgram of peptide-vinca drug conjugate and 150 micrograms of tissue protein, prepared as described in Step A and as determined by Bradford in reaction buffer are placed in solution of final volume of 200 microliters in buffer (50 mM TRIS, 140 mM NaCl, pH 7.2). Assay reactions are run for 0, 30, 60, 120, and 180 minutes and are then quenched with 9 microliters of 0.1 M $ZnCl_2$ and immediately placed in boiling water for 90 seconds. Reaction products are analyzed by HPLC using a VYDAC C18 15 cm column in water/acetonitrile (5% to 50% acetonitrile over 30 minutes).

What is claimed is:

1. A conjugate which is useful for the treatment of prostate cancer which comprises a vinca alkaloid cytotoxic agent attached to an oligopeptide, wherein the oligopeptide comprises a sequence of amino acids that is selectively proteolytically cleaved by free prostate specific antigen and wherein the means of attachment is through a diamine chemical linker which comprises a cycloalkyl or bicycloalkyl moiety, or the pharmaceutically acceptable salt thereof.

2. The conjugate according to claim 1 wherein the cytotoxic agent is selected from the following cytotoxic agents:
    a) vinblastine,
    b) 4-desacetylvinblastine,
    c) vincristine,
    d) leurosidine, and
    e) vindesine,
or the pharmaceutically acceptable salt thereof.

3. The conjugate according to claim 2 wherein the cytotoxic agent is selected from vinblastine and 4-desacetylvinblastine.

4. The conjugate according to claim 1 wherein the oligopeptide comprises an oligomer selected from the group consisting of:
a) AsnLysIleSerTyrGln|Ser (SEQ.ID.NO.: 1),
b) LysIleSerTyrGln|Ser (SEQ.ID.NO.: 2),
c) AsnLysIleSerTyrTyr|Ser (SEQ.ID.NO.: 3),
d) AsnLysAlaSerTyrGln|Ser (SEQ.ID.NO.: 4),
e) SerTyrGln|SerSer (SEQ.ID.NO.: 5);
f) LysTyrGln|SerSer (SEQ.ID.NO.: 6);
g) hArgTyrGln|SerSer (SEQ.ID.NO.: 7);
h) hArgChaGln|SerSer (SEQ.ID.NO.: 8);
i) TyrGln|SerSer (SEQ.ID.NO.: 9);
j) TyrGln|SerLeu (SEQ.ID.NO.: 10);
k) TyrGln|SerNle (SEQ.ID.NO.: 11);
l) ChgGln|SerLeu (SEQ.ID.NO.: 12);
m) ChgGln|SerNle (SEQ.ID.NO.: 13);
n) SerTyrGln|Ser (SEQ.ID.NO.: 14);
o) SerChgGln|Ser (SEQ.ID.NO.: 15);
p) SerTyrGln|SerVal (SEQ.ID.NO.: 16);
q) SerChgGln|SerVal (SEQ.ID.NO.: 17);
r) SerTyrGln|SerLeu (SEQ.ID.NO.: 18);
s) SerChgGln|SerLeu (SEQ.ID.NO.: 19);
t) HaaXaaSerTyrGln|Ser (SEQ.ID.NO.: 20);
u) HaaXaaLysTyrGln|Ser (SEQ.ID.NO.: 21);
v) HaaXaahArgTyrGln|Ser (SEQ.ID.NO.: 22);
w) HaaXaahArgChaGln|Ser (SEQ.ID.NO.: 23);
x) HaaTyrGln|Ser (SEQ.ID.NO.: 24);
y) HaaXaaSerChgGln|Ser (SEQ.ID.NO.: 25); and
z) HaaChgGln|Ser (SEQ.ID.NO.: 26);
wherein Haa is a cyclic amino acid substituted with a hydrophilic moiety, hArg is homoarginine, Xaa is any amino acid, Cha is cyclohexylalanine and Chg is cyclohexylglycine.

5. The conjugate according to claim 1 wherein the oligopeptide comprises an oligomer selected from:
SerSerChgGln|SerLeu (SEQ.ID.NO.: 39);
SerSerChgGln|SerVal (SEQ.ID.NO.: 40);
SerSerSerChgGln|SerLeu (SEQ.ID.NO.: 41);
SerSerSerChgGln|SerVal (SEQ.ID.NO.: 42);
SerAlaSerChgGln|SerLeu (SEQ.ID.NO.: 43);
SerAlaSerChgGln|SerVal (SEQ.ID.NO.: 44);
(N-methyl-Ser)SerSerChgGln|SerLeu (SEQ.ID.NO.: 45);
(N-methyl-Ser)SerSerChgGln|SerVal (SEQ.ID.NO.: 46);
4-HypSerSerTyrGln|SerVal (SEQ.ID.NO.: 47);
4-HypSerSerTyrGln|SerLeu (SEQ.ID.NO.: 48);
4-HypSerSerChgGln|SerVal (SEQ.ID.NO.: 49);
4-HypSerSerChgGln|SerLeu (SEQ.ID.NO.: 50);
4-HypAlaSerChgGln|SerVal (SEQ.ID.NO.: 51);
4-HypAlaSerChgGln|SerLeu (SEQ.ID.NO.: 52);
(3,4-DiHyp)SerSerTyrGln|SerVal (SEQ.ID.NO.: 53); and
(3,4-DiHyp)SerSerTyrGln|SerLeu (SEQ.ID.NO.: 54);
wherein 4-Hyp is 4-hydroxyproline, 3,4-DiHyp is 3,4-dihydroxyproline, N-methyl-Ser is cyclohexylalanine and Chg is cyclohexylglycine.

6. The conjugate according to claim 1 of the formula I:

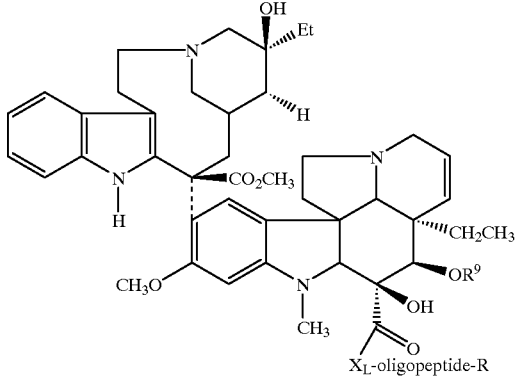

wherein:
oligopeptide is an oligopeptide which is specifically recognized by the free prostate specific antigen (PSA) and is capable of being proteolytically cleaved by the enzymatic activity of the free prostate specific antigen, $X_L$ is —NH—$(CH_2)_u$—W—$(CH_2)_u$—NH—

R is selected from
a) hydrogen,
b) —(C=O)$R^{1a}$, c) 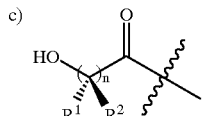

d) 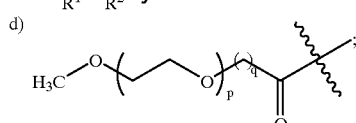

e) 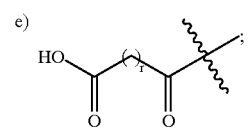

f) ethoxysquarate; and
g) cotininyl;

$R^1$ and $R^2$ are independently selected from: hydrogen, OH, $C_1$–$C_6$ alkyl, $C_1$–$C_6$ alkoxy, $C_1$–$C_6$ aralkyl and aryl;

$R^{1a}$ is $C_1$–$C_6$-alkyl or aryl, $R^{19}$ is hydrogen, ($C_1$–$C_3$ alkyl)-CO, or chlorosubstituted ($C_1$–$C_3$ alkyl)-CO;

W is selected from the group consisting of cyclopentyl, cyclohexyl, cycloheptyl and bicyclo[2.2.2]octanyl;

n is 1, 2, 3 or 4;
p is zero or an integer between 1 and 100;
q is 0 or 1, provided that if p is zero, q is 1;
r is 1, 2 or 3;
t is 3 or 4;
u is 0, 1, 2 or 3, or a pharmaceutically acceptable salt thereof.

7. The conjugate according to claim 6 wherein:
oligopeptide is an oligomer that comprises an amino acid sequence selected from the group consisting of:

a) AsnLysIleSerTyrGln|Ser (SEQ.ID.NO.: 1),
b) LysIleSerTyrGln|Ser (SEQ.ID.NO.: 2),
c) AsnLysIleSerTyrTyr|Ser (SEQ.ID.NO.: 3),
d) AsnLysAlaSerTyrGln|Ser (SEQ.ID.NO.: 4),
e) SerTyrGln|SerSer (SEQ.ID.NO.: 5);
f) LysTyrGln|SerSer (SEQ.ID.NO.: 6);
g) hArgTyrGln|SerSer (SEQ.ID.NO.: 7);
h) hArgChaGln|SerSer (SEQ.ID.NO.: 8);
i) TyrGln|SerSer (SEQ.ID.NO.: 9);
j) TyrGln|SerLeu (SEQ.ID.NO.: 10);
k) TyrGln|SerNle (SEQ.ID.NO.: 11);
l) ChgGln|SerLeu (SEQ.ID.NO.: 12);
m) ChgGln|SerNle (SEQ.ID.NO.: 13);
n) SerTyrGln|Ser (SEQ.ID.NO.: 14);
o) SerChgGln|Ser (SEQ.ID.NO.: 15);
p) SerTyrGln|SerVal (SEQ.ID.NO.: 16);
q) SerChgGln|SerVal (SEQ.ID.NO.: 17);
r) SerTyrGln|SerLeu (SEQ.ID.NO.: 18);
s) SerChgGln|SerLeu (SEQ.ID.NO.: 19);
t) HaaXaaSerTyrGln|Ser (SEQ.ID.NO.: 20);
u) HaaXaaLysTyrGln|Ser (SEQ.ID.NO.: 21);
v) HaaXaahArgTyrGln|Ser (SEQ.ID.NO.: 22);
w) HaaXaahArgChaGln|Ser (SEQ.ID.NO.: 23);
x) HaaTyrGln|Ser (SEQ.ID.NO.: 24);
y) HaaXaaSerChgGln|Ser (SEQ.ID.NO.: 25); and
z) HaaChgGln|Ser (SEQ.ID.NO.: 26);

wherein Haa is a cyclic amino acid substituted with a hydrophilic moiety, hArg is homoarginine, Xaa is any amino acid, Cha is cyclohexylalanine and Chg is cyclohexylglycine;

or an optical isomer or pharmaceutically acceptable salt thereof.

8. The conjugate according to claim 7 wherein:
Xaa is alanine, serine or isoleucine; and
Haa is trans-4-hydroxy-L-proline;

or an optical isomer or pharmaceutically acceptable salt thereof.

9. The conjugate according to claim 8 which is selected from the group consisting of:

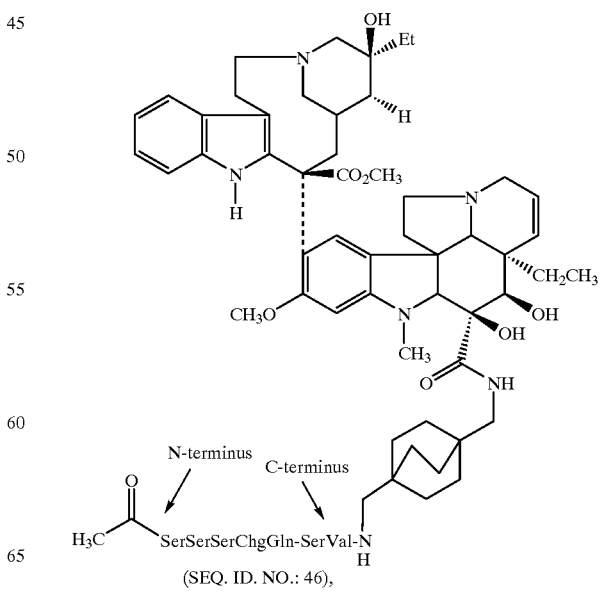

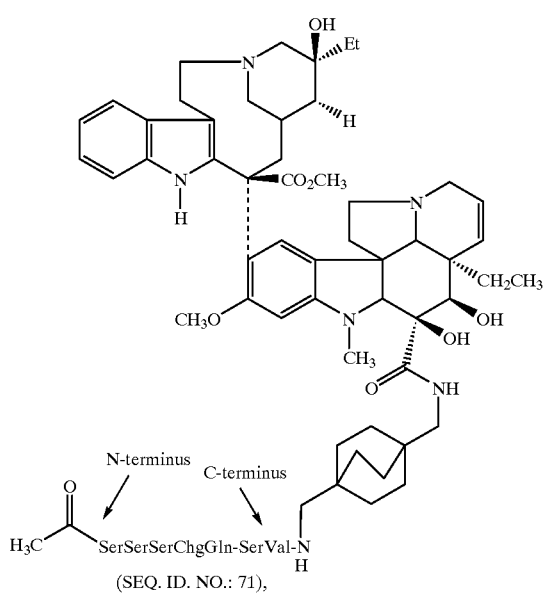
(SEQ. ID. NO.: 71),
and the pharmaceutically acceptable salts and optical isomer thereof.
10. The conjugate according to claim 8 which is selected from the group consisting of:
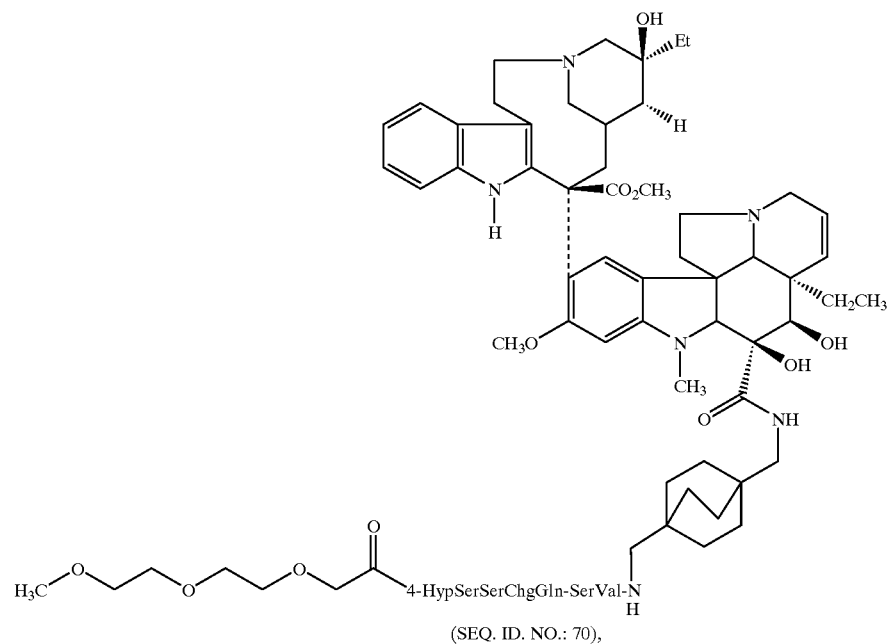
(SEQ. ID. NO.: 70),

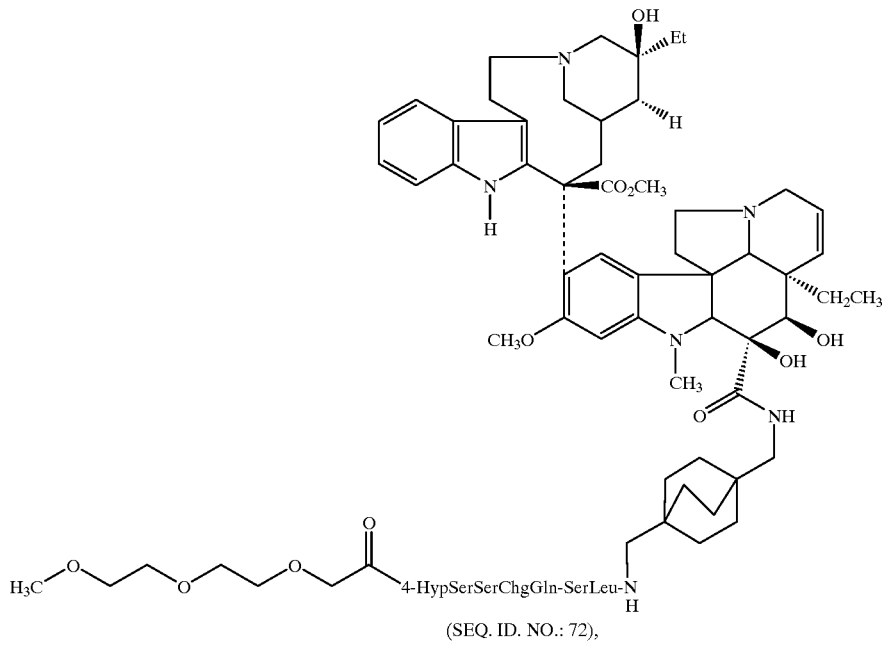

(SEQ. ID. NO.: 72), and the pharmaceutically acceptable salts and optical isomer thereof.

11. A pharmaceutical composition comprising a pharmaceutical carrier, and dispersed therein, a therapeutically effective amount of a compound of claim 6.

12. A method for treating prostate cancer which comprises administering to a mammal in need thereof a therapeutically effective amount of a composition of claim 11.

13. A method for treating benign prostatic hyperplasia which comprises administering to a mammal in need thereof a therapeutically effective amount of a composition of claim 11.

14. A pharmaceutical composition comprising a pharmaceutical carrier, and dispersed therein, a therapeutically effective amount of a compound of claim 1.

15. A method for treating prostate cancer which comprises administering to a mammal in need thereof a therapeutically effective amount of a composition of claim 14.

16. A method for treating benign prostatic hyperplasia which comprises administering to a mammal in need thereof a therapeutically effective amount of a composition of claim 14.

17. A process for making a pharmaceutical composition comprising combining a compound of claim 1 and a pharmaceutically acceptable carrier.

18. A compound which is selected from the group consisting of:
Ac-SerSerSerChgGln-SerVal-DAP(dAc)VIN (SEQ.ID.NO.: 73)
Ac-ProSerSerChgGln-SerVal-DAP(dAc)VIN (SEQ.ID.NO.: 74)
Ac-SerSerSerChgGlnSerVal-1,4-BDAM-(dAc)-VIN (SEQ.ID.NO.: 73)
Ac-SerSerSerChgGln-Ser(dVal)-1,4-BDAM-(dAc)-VIN (SEQ.ID.NO.: 75)
Ac-SerSerSerChgGln-Ser-BDAM-(dAc)-VIN (SEQ.ID.NO.: 76)
(2-OH)Ac-(4-trans-L-Hyp)SerSerChgGln-SerVal-BDAM-(dAc)-VIN (SEQ.ID.NO.: 77)
PEG(2)-(4-trans-L-Hyp)-SerSerChgGlnSerVal-BDAM-(dAc)-VIN (SEQ.ID.NO.: 78)
PEG(2)-3,4-(diOH)Pro-SerSerChgGln-SerVal-BDAM-(dAc)-VIN (SEQ.ID.NO.: 79)
Ac-3,4-(diOH)ProSerSerChgGln-SerVal-BDAM-(dAc)-VIN (SEQ.ID.NO.: 80)
Succinyl-(4-trans-L-Hyp)SerSerChgGln-SerVal-BDAM-(dAc)-VIN (SEQ.ID.NO.: 81)
PEG(2)-(N-Me-Ser)SerSerChgGln-SerVal-BDAM-(dAc)-VIN (SEQ.ID.NO.: 82)
(N-Me-Ser)SerSerChgGln-SerVal-BDAM-(dAc)-VIN (SEQ.ID.NO.: 83)
Quinyl-SerSerSerChgGln-SerVal-BDAM-(dAc)-VIN (SEQ.ID.NO.: 84)
Gallyl-SerSerSerChgGln-SerVal-BDAM-(dAc)-VIN (SEQ.ID.NO.: 85)
Ac-keto-(4-trans-L-Hyp)SerSerChgGln-SerVal-BDAM-(dAc)-VIN (SEQ.ID.NO.: 103)
PEG(2)-(4-trans-L-Hyp)AlaSerChgGln-SerVal-BDAM-(dAc)-VIN (SEQ.ID.NO.: 86)
4-imidazoleacetyl-(4-trans-L-Hyp)SerSerChgGlnSerVal-BDAM-(dAc)-VIN (SEQ.ID.NO.: 87)
Ac-HisAlaSerChgGlnSerVal-BDAM-(dAc)-VIN (SEQ.ID.NO.: 88)
PEG(2)-C(SO3)-SerSerChgGlnSerVal-BDAM-(dAc)-VIN (SEQ.ID.NO.: 89)
Gulonic-(4-trans-L-Hyp)-SerSerChgGlnSerVal-BDAM-(dAc)-VIN (SEQ.ID.NO.: 90)
4-phosphonylbutylryl-(4-trans-L-Hyp) SerSerChgGlnSerVal-BDAM-(dAc)-VIN (SEQ.ID.NO.: 91)
Cotininyl-(4-trans-L-Hyp)SerSerChgGlnSerVal-BDAM-(dAc)-VIN (SEQ.ID.NO.: 92)
3-phosphonylpropionyl-(4-trans-L-Hyp) SerSerChgGlnSerVal-BDAM-(dAc)-VIN (SEQ.ID.NO.: 93)
Succinyl-(4-trans-L-Hyp)SerSerChgGln-SerVal-BDAM-(dAc)-VIN (SEQ.ID.NO.: 94)
Glutaryl-(4-trans-L-Hyp)SerSerChgGln-SerVal-BDAM-(dAc)-VIN (SEQ.ID.NO.: 95)
Ethoxysquarate-(4-trans-L-Hyp)SerSerChgGln-SerVal-BDAM-(dAc)-VIN (SEQ.ID.NO.: 96)

PEG2-(4-trans-L-Hyp)SerSerChgGlnSerLeu-BDAM-(dAc)-VIN (SEQ.ID.NO.: 97)
Ac-SerSerSerChgGlnSerLeu-BDAM-(dAc)-VIN (SEQ.ID.NO.: 98)
Ac-HisSerSerChgGlnSerLeu-BDAM-(dAc)-VIN (SEQ.ID.NO.: 99), and
Glutaryl-(4-trans-L-Hyp)ASerChgGln-SerLeu-BDAM-(dAc)-VIN (SEQ.ID.NO.: 100)
or the pharmaceutically acceptable salts and optical isomers thereof.

19. A pharmaceutical composition comprising a pharmaceutical carrier, and dispersed therein, a therapeutically effective amount of a compound of claim 18.

20. A method for treating prostate cancer which comprises administering to a mammal in need thereof a therapeutically effective amount of a composition of claim 19.

21. A method for treating benign prostatic hyperplasia which comprises administering to a mammal in need thereof a therapeutically effective amount of a composition of claim 19.

* * * * *

SEQUENCE LISTING

<160> NUMBER OF SEQ ID NOS: 103

<210> SEQ ID NO 1
<211> LENGTH: 7
<212> TYPE: PRT
<213> ORGANISM: Artificial Sequence
<220> FEATURE:
<223> OTHER INFORMATION: completely synthetic amino acid sequence

<400> SEQUENCE: 1

Asn Lys Ile Ser Tyr Gln Ser
 1               5

<210> SEQ ID NO 2
<211> LENGTH: 6
<212> TYPE: PRT
<213> ORGANISM: Artificial Sequence
<220> FEATURE:
<223> OTHER INFORMATION: completely synthetic amino acid sequence

<400> SEQUENCE: 2

Lys Ile Ser Tyr Gln Ser
 1               5

<210> SEQ ID NO 3
<211> LENGTH: 7
<212> TYPE: PRT
<213> ORGANISM: Artificial Sequence
<220> FEATURE:
<223> OTHER INFORMATION: completely synthetic amino acid sequence

<400> SEQUENCE: 3

Asn Lys Ile Ser Tyr Tyr Ser
 1               5

<210> SEQ ID NO 4
<211> LENGTH: 7
<212> TYPE: PRT
<213> ORGANISM: Artificial Sequence
<220> FEATURE:
<223> OTHER INFORMATION: completely synthetic amino acid sequence

<400> SEQUENCE: 4

Asn Lys Ala Ser Tyr Gln Ser
 1               5

<210> SEQ ID NO 5
<211> LENGTH: 5
<212> TYPE: PRT
<213> ORGANISM: Artificial Sequence
<220> FEATURE:
<223> OTHER INFORMATION: completely synthetic amino acid sequence

<400> SEQUENCE: 5

Ser Tyr Gln Ser Ser
 1               5

<210> SEQ ID NO 6
<211> LENGTH: 5
<212> TYPE: PRT
<213> ORGANISM: Artificial Sequence
<220> FEATURE:
<223> OTHER INFORMATION: completely synthetic amino acid sequence

<400> SEQUENCE: 6

```
Lys Tyr Gln Ser Ser
 1               5

<210> SEQ ID NO 7
<211> LENGTH: 5
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: MOD_RES
<222> LOCATION: (1)...(1)
<223> OTHER INFORMATION: homoarginine

<400> SEQUENCE: 7

Xaa Tyr Gln Ser Ser
 1               5

<210> SEQ ID NO 8
<211> LENGTH: 5
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: MOD_RES
<222> LOCATION: (1)...(1)
<223> OTHER INFORMATION: homoarginine
<220> FEATURE:
<221> NAME/KEY: MOD_RES
<222> LOCATION: (2)...(2)
<223> OTHER INFORMATION: cyclohexylalanine

<400> SEQUENCE: 8

Xaa Xaa Gln Ser Ser
 1               5

<210> SEQ ID NO 9
<211> LENGTH: 4
<212> TYPE: PRT
<213> ORGANISM: Artificial Sequence
<220> FEATURE:
<223> OTHER INFORMATION: completely synthetic amino acid sequence

<400> SEQUENCE: 9

Tyr Gln Ser Ser
 1

<210> SEQ ID NO 10
<211> LENGTH: 4
<212> TYPE: PRT
<213> ORGANISM: Artificial Sequence
<220> FEATURE:
<223> OTHER INFORMATION: completely synthetic amino acid sequence

<400> SEQUENCE: 10

Tyr Gln Ser Leu
 1

<210> SEQ ID NO 11
<211> LENGTH: 4
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: MOD_RES
<222> LOCATION: (4)...(4)
<223> OTHER INFORMATION: norleucine
```

```
<400> SEQUENCE: 11

Tyr Gln Ser Leu
 1

<210> SEQ ID NO 12
<211> LENGTH: 4
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (1)...(1)
<223> OTHER INFORMATION: cyclohexylglycine

<400> SEQUENCE: 12

Xaa Gln Ser Leu
 1

<210> SEQ ID NO 13
<211> LENGTH: 4
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (1)...(1)
<223> OTHER INFORMATION: cyclohexylglycine
<220> FEATURE:
<221> NAME/KEY: MOD_RES
<222> LOCATION: (4)...(4)
<223> OTHER INFORMATION: norleucine

<400> SEQUENCE: 13

Xaa Gln Ser Leu
 1

<210> SEQ ID NO 14
<211> LENGTH: 4
<212> TYPE: PRT
<213> ORGANISM: Artificial Sequence
<220> FEATURE:
<223> OTHER INFORMATION: completely synthetic amino acid sequence

<400> SEQUENCE: 14

Ser Tyr Gln Ser
 1

<210> SEQ ID NO 15
<211> LENGTH: 4
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (2)...(2)
<223> OTHER INFORMATION: cyclohexylglycine

<400> SEQUENCE: 15

Ser Xaa Gln Ser
 1

<210> SEQ ID NO 16
<211> LENGTH: 5
<212> TYPE: PRT
<213> ORGANISM: Artificial Sequence
<220> FEATURE:
```

<223> OTHER INFORMATION: completely synthetic amino acid sequence

<400> SEQUENCE: 16

Ser Tyr Gln Ser Val
1               5

<210> SEQ ID NO 17
<211> LENGTH: 5
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (2)...(2)
<223> OTHER INFORMATION: cyclohexylglycine

<400> SEQUENCE: 17

Ser Xaa Gln Ser Val
1               5

<210> SEQ ID NO 18
<211> LENGTH: 5
<212> TYPE: PRT
<213> ORGANISM: Artificial Sequence
<220> FEATURE:
<223> OTHER INFORMATION: completely synthetic amino acid sequence

<400> SEQUENCE: 18

Ser Tyr Gln Ser Leu
1               5

<210> SEQ ID NO 19
<211> LENGTH: 5
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (2)...(2)
<223> OTHER INFORMATION: cyclohexylglycine

<400> SEQUENCE: 19

Ser Xaa Gln Ser Leu
1               5

<210> SEQ ID NO 20
<211> LENGTH: 6
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (1)...(1)
<223> OTHER INFORMATION: cyclic amino acid substituted with a
      hydrophilic moiety
<220> FEATURE:
<221> NAME/KEY: VARIANT
<222> LOCATION: (2)...(2)
<223> OTHER INFORMATION: any amino acid

<400> SEQUENCE: 20

Xaa Xaa Ser Tyr Gln Ser
1               5

<210> SEQ ID NO 21
<211> LENGTH: 6

```
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (1)...(1)
<223> OTHER INFORMATION: cyclic amino acid substituted with a
      hydrophilic moiety
<220> FEATURE:
<221> NAME/KEY: VARIANT
<222> LOCATION: (2)...(2)
<223> OTHER INFORMATION: any amino acid

<400> SEQUENCE: 21

Xaa Xaa Lys Tyr Gln Ser
 1               5

<210> SEQ ID NO 22
<211> LENGTH: 6
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (1)...(1)
<223> OTHER INFORMATION: cyclic amino acid substituted with a
      hydrophilic moiety
<220> FEATURE:
<221> NAME/KEY: VARIANT
<222> LOCATION: (3)...(3)
<223> OTHER INFORMATION: homoarginine
<220> FEATURE:
<221> NAME/KEY: VARIANT
<222> LOCATION: (2)...(2)
<223> OTHER INFORMATION: any amino acid

<400> SEQUENCE: 22

Xaa Xaa Xaa Tyr Gln Ser
 1               5

<210> SEQ ID NO 23
<211> LENGTH: 6
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (1)...(1)
<223> OTHER INFORMATION: cyclic amino acid substituted with a
      hydrophilic moiety
<220> FEATURE:
<221> NAME/KEY: VARIANT
<222> LOCATION: (3)...(3)
<223> OTHER INFORMATION: homoarginine
<220> FEATURE:
<221> NAME/KEY: VARIANT
<222> LOCATION: (4)...(4)
<223> OTHER INFORMATION: cyclohexylalanine
<220> FEATURE:
<221> NAME/KEY: VARIANT
<222> LOCATION: (2)...(2)
<223> OTHER INFORMATION: any amino acid

<400> SEQUENCE: 23

Xaa Xaa Xaa Xaa Gln Ser
 1               5

<210> SEQ ID NO 24
<211> LENGTH: 4
<212> TYPE: PRT
```

```
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (1)...(1)
<223> OTHER INFORMATION: cyclic amino acid substituted with a
      hydrophilic moiety

<400> SEQUENCE: 24

Xaa Tyr Gln Ser
 1

<210> SEQ ID NO 25
<211> LENGTH: 6
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (1)...(1)
<223> OTHER INFORMATION: cyclic amino acid substituted with a
      hydrophilic moiety
<220> FEATURE:
<221> NAME/KEY: VARIANT
<222> LOCATION: (4)...(4)
<223> OTHER INFORMATION: cyclohexylglycine
<220> FEATURE:
<221> NAME/KEY: VARIANT
<222> LOCATION: (2)...(2)
<223> OTHER INFORMATION: any amino acid

<400> SEQUENCE: 25

Xaa Xaa Ser Xaa Gln Ser
 1               5

<210> SEQ ID NO 26
<211> LENGTH: 4
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (1)...(1)
<223> OTHER INFORMATION: cyclic amino acid substituted with a
      hydrophilic moiety
<220> FEATURE:
<221> NAME/KEY: VARIANT
<222> LOCATION: (2)...(2)
<223> OTHER INFORMATION: cyclohexylglycine

<400> SEQUENCE: 26

Xaa Xaa Gln Ser
 1

<210> SEQ ID NO 27
<211> LENGTH: 6
<212> TYPE: PRT
<213> ORGANISM: Artificial Sequence
<220> FEATURE:
<223> OTHER INFORMATION: completely synthetic amino acid sequence

<400> SEQUENCE: 27

Ser Ser Tyr Gln Ser Val
 1               5

<210> SEQ ID NO 28
<211> LENGTH: 6
<212> TYPE: PRT
```

```
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (3)...(3)
<223> OTHER INFORMATION: cyclohexylglycine

<400> SEQUENCE: 28

Ser Ser Xaa Gln Ser Val
 1               5

<210> SEQ ID NO 29
<211> LENGTH: 6
<212> TYPE: PRT
<213> ORGANISM: Artificial Sequence
<220> FEATURE:
<223> OTHER INFORMATION: completely synthetic amino acid sequence

<400> SEQUENCE: 29

Ser Ser Tyr Gln Ser Leu
 1               5

<210> SEQ ID NO 30
<211> LENGTH: 6
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (3)...(3)
<223> OTHER INFORMATION: cyclohexylglycine

<400> SEQUENCE: 30

Ser Ser Xaa Gln Ser Leu
 1               5

<210> SEQ ID NO 31
<211> LENGTH: 6
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: MOD_RES
<222> LOCATION: (1)...(1)
<223> OTHER INFORMATION: 4Hyp

<400> SEQUENCE: 31

Pro Ser Ser Tyr Gln Ser
 1               5

<210> SEQ ID NO 32
<211> LENGTH: 6
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: MOD_RES
<222> LOCATION: (1)...(1)
<223> OTHER INFORMATION: 4Hyp
<220> FEATURE:
<221> NAME/KEY: VARIANT
<222> LOCATION: (4)...(4)
<223> OTHER INFORMATION: cyclohexylglycine

<400> SEQUENCE: 32

Pro Ser Ser Xaa Gln Ser
```

```
                                 1               5

<210> SEQ ID NO 33
<211> LENGTH: 6
<212> TYPE: PRT
<213> ORGANISM: Artificial Sequence
<220> FEATURE:
<223> OTHER INFORMATION: completely synthetic amino acid sequence

<400> SEQUENCE: 33

Ala Ser Tyr Gln Ser Val
 1               5

<210> SEQ ID NO 34
<211> LENGTH: 6
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (3)...(3)
<223> OTHER INFORMATION: cyclohexylglycine

<400> SEQUENCE: 34

Ala Ser Xaa Gln Ser Val
 1               5

<210> SEQ ID NO 35
<211> LENGTH: 6
<212> TYPE: PRT
<213> ORGANISM: Artificial Sequence
<220> FEATURE:
<223> OTHER INFORMATION: completely synthetic amino acid sequence

<400> SEQUENCE: 35

Ala Ser Tyr Gln Ser Leu
 1               5

<210> SEQ ID NO 36
<211> LENGTH: 6
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (3)...(3)
<223> OTHER INFORMATION: cyclohexylglycine

<400> SEQUENCE: 36

Ala Ser Xaa Gln Ser Leu
 1               5

<210> SEQ ID NO 37
<211> LENGTH: 6
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: MOD_RES
<222> LOCATION: (1)...(1)
<223> OTHER INFORMATION: 4Hyp

<400> SEQUENCE: 37

Pro Ala Ser Tyr Gln Ser
 1               5
```

```
<210> SEQ ID NO 38
<211> LENGTH: 6
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: MOD_RES
<222> LOCATION: (1)...(1)
<223> OTHER INFORMATION: 4Hyp
<220> FEATURE:
<221> NAME/KEY: VARIANT
<222> LOCATION: (4)...(4)
<223> OTHER INFORMATION: cyclohexylglycine

<400> SEQUENCE: 38

Pro Ala Ser Xaa Gln Ser
 1               5

<210> SEQ ID NO 39
<211> LENGTH: 6
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (3)...(3)
<223> OTHER INFORMATION: cyclohexylglycine

<400> SEQUENCE: 39

Ser Ser Xaa Gln Ser Leu
 1               5

<210> SEQ ID NO 40
<211> LENGTH: 6
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (3)...(3)
<223> OTHER INFORMATION: cyclohexylglycine

<400> SEQUENCE: 40

Ser Ser Xaa Gln Ser Val
 1               5

<210> SEQ ID NO 41
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (4)...(4)
<223> OTHER INFORMATION: cyclohexylglycine

<400> SEQUENCE: 41

Ser Ser Ser Xaa Gln Ser Leu
 1               5

<210> SEQ ID NO 42
<211> LENGTH: 7
<212> TYPE: PRT
<213> ORGANISM: Artificial Sequence
<220> FEATURE:
<223> OTHER INFORMATION: completely synthetic amino acid sequence
```

```
<220> FEATURE:
<221> NAME/KEY: VARIANT
<222> LOCATION: (4)...(4)
<223> OTHER INFORMATION: cyclohexylglycine

<400> SEQUENCE: 42

Ser Ser Ser Xaa Gln Ser Val
 1               5

<210> SEQ ID NO 43
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (4)...(4)
<223> OTHER INFORMATION: cyclohexylglycine

<400> SEQUENCE: 43

Ser Ala Ser Xaa Gln Ser Leu
 1               5

<210> SEQ ID NO 44
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: CONFLICT
<222> LOCATION: (4)...(4)
<223> OTHER INFORMATION: cyclohexylglycine

<400> SEQUENCE: 44

Ser Ala Ser Xaa Gln Ser Val
 1               5

<210> SEQ ID NO 45
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: METHYLATION
<222> LOCATION: (1)...(1)
<223> OTHER INFORMATION: N-methylserine
<220> FEATURE:
<221> NAME/KEY: VARIANT
<222> LOCATION: (4)...(4)
<223> OTHER INFORMATION: cyclohexylglycine

<400> SEQUENCE: 45

Xaa Ser Ser Xaa Gln Ser Leu
 1               5

<210> SEQ ID NO 46
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: METHYLATION
<222> LOCATION: (1)...(1)
<223> OTHER INFORMATION: N-methylserine
<220> FEATURE:
<221> NAME/KEY: VARIANT
<222> LOCATION: (4)...(4)
```

```
<223> OTHER INFORMATION: cyclohexylglycine

<400> SEQUENCE: 46

Xaa Ser Ser Xaa Gln Ser Val
 1               5

<210> SEQ ID NO 47
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: MOD_RES
<222> LOCATION: (1)...(1)
<223> OTHER INFORMATION: 4Hyp

<400> SEQUENCE: 47

Pro Ser Ser Tyr Gln Ser Val
 1               5

<210> SEQ ID NO 48
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: MOD_RES
<222> LOCATION: (1)...(1)
<223> OTHER INFORMATION: 4Hyp

<400> SEQUENCE: 48

Pro Ser Ser Tyr Gln Ser Leu
 1               5

<210> SEQ ID NO 49
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: MOD_RES
<222> LOCATION: (1)...(1)
<223> OTHER INFORMATION: 4Hyp
<220> FEATURE:
<221> NAME/KEY: VARIANT
<222> LOCATION: (4)...(4)
<223> OTHER INFORMATION: cyclohexylglycine

<400> SEQUENCE: 49

Pro Ser Ser Xaa Gln Ser Val
 1               5

<210> SEQ ID NO 50
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: MOD_RES
<222> LOCATION: (1)...(1)
<223> OTHER INFORMATION: 4Hyp
<220> FEATURE:
<221> NAME/KEY: VARIANT
<222> LOCATION: (4)...(4)
<223> OTHER INFORMATION: cyclohexylglycine

<400> SEQUENCE: 50
```

```
Pro Ser Ser Xaa Gln Ser Leu
1               5
```

<210> SEQ ID NO 51
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: MOD_RES
<222> LOCATION: (1)...(1)
<223> OTHER INFORMATION: 4Hyp
<220> FEATURE:
<221> NAME/KEY: VARIANT
<222> LOCATION: (4)...(4)
<223> OTHER INFORMATION: cyclohexylglycine

<400> SEQUENCE: 51

```
Pro Ala Ser Xaa Gln Ser Val
1               5
```

<210> SEQ ID NO 52
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: MOD_RES
<222> LOCATION: (1)...(1)
<223> OTHER INFORMATION: 4Hyp
<220> FEATURE:
<221> NAME/KEY: VARIANT
<222> LOCATION: (4)...(4)
<223> OTHER INFORMATION: cyclohexylglycine

<400> SEQUENCE: 52

```
Pro Ala Ser Xaa Gln Ser Leu
1               5
```

<210> SEQ ID NO 53
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (1)...(1)
<223> OTHER INFORMATION: 3,4-dihydroxyproline

<400> SEQUENCE: 53

```
Xaa Ser Ser Tyr Gln Ser Val
1               5
```

<210> SEQ ID NO 54
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (1)...(1)
<223> OTHER INFORMATION: 3,4-dihydroxyproline

<400> SEQUENCE: 54

```
Xaa Ser Ser Tyr Gln Ser Val
1               5
```

```
<210> SEQ ID NO 55
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (1)...(1)
<223> OTHER INFORMATION: homoarginine
<220> FEATURE:
<221> NAME/KEY: VARIANT
<222> LOCATION: (4)...(4)
<223> OTHER INFORMATION: cyclohexylglycine

<400> SEQUENCE: 55

Xaa Ser Ala Xaa Gln Ser Leu
 1               5

<210> SEQ ID NO 56
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (1)...(1)
<223> OTHER INFORMATION: homoarginine
<220> FEATURE:
<221> NAME/KEY: MOD_RES
<222> LOCATION: (3)...(3)
<223> OTHER INFORMATION: 4Hyp
<220> FEATURE:
<221> NAME/KEY: VARIANT
<222> LOCATION: (4)...(4)
<223> OTHER INFORMATION: cyclohexylglycine

<400> SEQUENCE: 56

Xaa Ser Pro Xaa Gln Ser Leu
 1               5

<210> SEQ ID NO 57
<211> LENGTH: 5
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: MOD_RES
<222> LOCATION: (1)...(1)
<223> OTHER INFORMATION: 4Hyp
<220> FEATURE:
<221> NAME/KEY: VARIANT
<222> LOCATION: (2)...(2)
<223> OTHER INFORMATION: cyclohexylglycine

<400> SEQUENCE: 57

Pro Xaa Gln Ser Leu
 1               5

<210> SEQ ID NO 58
<211> LENGTH: 7
<212> TYPE: PRT
<213> ORGANISM: Artificial Sequence
<220> FEATURE:
<223> OTHER INFORMATION: completely synthetic amino acid sequence

<400> SEQUENCE: 58

Asn Arg Ile Ser Tyr Gln Ser
```

```
                1               5

<210> SEQ ID NO 59
<211> LENGTH: 7
<212> TYPE: PRT
<213> ORGANISM: Artificial Sequence
<220> FEATURE:
<223> OTHER INFORMATION: completely synthetic amino acid sequence

<400> SEQUENCE: 59

Asn Lys Val Ser Tyr Gln Ser
 1               5

<210> SEQ ID NO 60
<211> LENGTH: 8
<212> TYPE: PRT
<213> ORGANISM: Artificial Sequence
<220> FEATURE:
<223> OTHER INFORMATION: completely synthetic amino acid sequence

<400> SEQUENCE: 60

Asn Lys Met Ser Tyr Gln Ser Ser
 1               5

<210> SEQ ID NO 61
<211> LENGTH: 8
<212> TYPE: PRT
<213> ORGANISM: Artificial Sequence
<220> FEATURE:
<223> OTHER INFORMATION: completely synthetic amino acid sequence

<400> SEQUENCE: 61

Asn Lys Leu Ser Tyr Gln Ser Ser
 1               5

<210> SEQ ID NO 62
<211> LENGTH: 7
<212> TYPE: PRT
<213> ORGANISM: Artificial Sequence
<220> FEATURE:
<223> OTHER INFORMATION: completely synthetic amino acid sequence

<400> SEQUENCE: 62

Asn Lys Ile Ser Tyr Gln Ser
 1               5

<210> SEQ ID NO 63
<211> LENGTH: 8
<212> TYPE: PRT
<213> ORGANISM: Artificial Sequence
<220> FEATURE:
<223> OTHER INFORMATION: completely synthetic amino acid sequence

<400> SEQUENCE: 63

Gln Lys Ile Ser Tyr Gln Ser Ser
 1               5

<210> SEQ ID NO 64
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: MOD_RES
<222> LOCATION: (2)...(2)
<223> OTHER INFORMATION: 4Hyp
```

```
<400> SEQUENCE: 64

Asn Pro Ile Ser Tyr Gln Ser
 1               5

<210> SEQ ID NO 65
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: MOD_RES
<222> LOCATION: (2)...(2)
<223> OTHER INFORMATION: 4Hyp

<400> SEQUENCE: 65

Asn Pro Val Ser Tyr Gln Ser
 1               5

<210> SEQ ID NO 66
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: MOD_RES
<222> LOCATION: (1)...(1)
<223> OTHER INFORMATION: 4Hyp

<400> SEQUENCE: 66

Pro Ala Ser Tyr Gln Ser Ser
 1               5

<210> SEQ ID NO 67
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (1)...(1)
<223> OTHER INFORMATION: 3,4-dihydroxyproline

<400> SEQUENCE: 67

Xaa Ala Ser Tyr Gln Ser Ser
 1               5

<210> SEQ ID NO 68
<211> LENGTH: 5
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: MOD_RES
<222> LOCATION: (1)...(1)
<223> OTHER INFORMATION: 3Hyp
<220> FEATURE:
<221> NAME/KEY: VARIANT
<222> LOCATION: (3)...(3)
<223> OTHER INFORMATION: cyclohexylglycine

<400> SEQUENCE: 68

Pro Ser Xaa Gln Ser
 1               5

<210> SEQ ID NO 69
```

```
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: MOD_RES
<222> LOCATION: (1)...(1)
<223> OTHER INFORMATION: 4Hyp
<220> FEATURE:
<221> NAME/KEY: VARIANT
<222> LOCATION: (4)...(4)
<223> OTHER INFORMATION: cyclohexylglycine

<400> SEQUENCE: 69

Pro Ala Ser Xaa Gln Ser Ser
 1               5

<210> SEQ ID NO 70
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (1)...(1)
<223> OTHER INFORMATION: N-(PEG-2)-4-hydroxyproline
<220> FEATURE:
<221> NAME/KEY: VARIANT
<222> LOCATION: (4)...(4)
<223> OTHER INFORMATION: cyclohexylglycine

<400> SEQUENCE: 70

Xaa Ser Ser Xaa Gln Ser Val
 1               5

<210> SEQ ID NO 71
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: ACETYLATION
<222> LOCATION: (1)...(1)
<223> OTHER INFORMATION: N-acetylserine
<220> FEATURE:
<221> NAME/KEY: VARIANT
<222> LOCATION: (4)...(4)
<223> OTHER INFORMATION: cyclohexylglycine

<400> SEQUENCE: 71

Xaa Ser Ser Xaa Gln Ser Leu
 1               5

<210> SEQ ID NO 72
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (1)...(1)
<223> OTHER INFORMATION: N-(PEG-2)-4-hydroxyproline
<220> FEATURE:
<221> NAME/KEY: VARIANT
<222> LOCATION: (4)...(4)
<223> OTHER INFORMATION: cyclohexylglycine

<400> SEQUENCE: 72
```

Xaa Ser Ser Xaa Gln Ser Leu
1               5

<210> SEQ ID NO 73
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: ACETYLATION
<222> LOCATION: (1)...(1)
<223> OTHER INFORMATION: N-acetylserine
<220> FEATURE:
<221> NAME/KEY: VARIANT
<222> LOCATION: (4)...(4)
<223> OTHER INFORMATION: cyclohexylglycine

<400> SEQUENCE: 73

Xaa Ser Ser Xaa Gln Ser Val
1               5

<210> SEQ ID NO 74
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: ACETYLATION
<222> LOCATION: (1)...(1)
<223> OTHER INFORMATION: N-acetylproline
<220> FEATURE:
<221> NAME/KEY: VARIANT
<222> LOCATION: (4)...(4)
<223> OTHER INFORMATION: cyclohexylglycine

<400> SEQUENCE: 74

Xaa Ser Ser Xaa Gln Ser Val
1               5

<210> SEQ ID NO 75
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: ACETYLATION
<222> LOCATION: (1)...(1)
<223> OTHER INFORMATION: N-acetylserine
<220> FEATURE:
<221> NAME/KEY: VARIANT
<222> LOCATION: (4)...(4)
<223> OTHER INFORMATION: cyclohexylglycine
<220> FEATURE:
<221> NAME/KEY: VARIANT
<222> LOCATION: (7)...(7)
<223> OTHER INFORMATION: valine having the unnatural configuration

<400> SEQUENCE: 75

Xaa Ser Ser Xaa Gln Ser Xaa
1               5

<210> SEQ ID NO 76
<211> LENGTH: 6
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: ACETYLATION

```
<222> LOCATION: (1)...(1)
<223> OTHER INFORMATION: N-acetylserine
<220> FEATURE:
<221> NAME/KEY: VARIANT
<222> LOCATION: (4)...(4)
<223> OTHER INFORMATION: cyclohexylglycine

<400> SEQUENCE: 76

Xaa Ser Ser Xaa Gln Ser
 1               5

<210> SEQ ID NO 77
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (1)...(1)
<223> OTHER INFORMATION: N-hydroxyacetyl-4-hydroxyproline
<220> FEATURE:
<221> NAME/KEY: VARIANT
<222> LOCATION: (4)...(4)
<223> OTHER INFORMATION: cyclohexylglycine

<400> SEQUENCE: 77

Xaa Ser Ser Xaa Gln Ser Val
 1               5

<210> SEQ ID NO 78
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (1)...(1)
<223> OTHER INFORMATION: N-(PEG)-4-hydroxyproline
<220> FEATURE:
<221> NAME/KEY: VARIANT
<222> LOCATION: (4)...(4)
<223> OTHER INFORMATION: cyclohexylglycine

<400> SEQUENCE: 78

Xaa Ser Ser Xaa Gln Ser Val
 1               5

<210> SEQ ID NO 79
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (1)...(1)
<223> OTHER INFORMATION: N-(PEG-2)-3,4-dihydroxyproline
<220> FEATURE:
<221> NAME/KEY: VARIANT
<222> LOCATION: (4)...(4)
<223> OTHER INFORMATION: cyclohexylglycine

<400> SEQUENCE: 79

Xaa Ser Ser Xaa Gln Ser Val
 1               5

<210> SEQ ID NO 80
<211> LENGTH: 7
<212> TYPE: PRT
```

```
<213> ORGANISM: Artificial Sequence
<220> FEATURE:
<223> OTHER INFORMATION: completely synthetic amino acid sequence
<220> FEATURE:
<221> NAME/KEY: ACETYLATION
<222> LOCATION: (1)...(1)
<223> OTHER INFORMATION: N-acetyl-3,4-dihydroxyproline
<220> FEATURE:
<221> NAME/KEY: VARIANT
<222> LOCATION: (4)...(4)
<223> OTHER INFORMATION: cyclohexylglycine
<220> FEATURE:
<221> NAME/KEY: VARIANT
<222> LOCATION: (7)...(7)
<223> OTHER INFORMATION: 2-amino-4,4-dimethylpropanoic acid

<400> SEQUENCE: 80

Xaa Ser Ser Xaa Gln Ser Val
 1               5

<210> SEQ ID NO 81
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (1)...(1)
<223> OTHER INFORMATION: N-succinyl-trans-4-hydroxyproline
<220> FEATURE:
<221> NAME/KEY: VARIANT
<222> LOCATION: (4)...(4)
<223> OTHER INFORMATION: cyclohexylglycine

<400> SEQUENCE: 81

Xaa Ser Ser Xaa Gln Ser Val
 1               5

<210> SEQ ID NO 82
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (1)...(1)
<223> OTHER INFORMATION: N-(PEG-2)-N-methylserine
<220> FEATURE:
<221> NAME/KEY: VARIANT
<222> LOCATION: (4)...(4)
<223> OTHER INFORMATION: cyclohexylglycine

<400> SEQUENCE: 82

Xaa Ser Ser Xaa Gln Ser Val
 1               5

<210> SEQ ID NO 83
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: METHYLATION
<222> LOCATION: (1)...(1)
<223> OTHER INFORMATION: N-methylserine
<220> FEATURE:
<221> NAME/KEY: VARIANT
<222> LOCATION: (4)...(4)
<223> OTHER INFORMATION: cyclohexylglycine
```

<400> SEQUENCE: 83

Xaa Ser Ser Xaa Gln Ser Val
1               5

<210> SEQ ID NO 84
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (1)...(1)
<223> OTHER INFORMATION: N-quinylserine
<220> FEATURE:
<221> NAME/KEY: VARIANT
<222> LOCATION: (4)...(4)
<223> OTHER INFORMATION: cyclohexylglycine

<400> SEQUENCE: 84

Xaa Ser Ser Xaa Gln Ser Val
1               5

<210> SEQ ID NO 85
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (1)...(1)
<223> OTHER INFORMATION: N-gallylserine
<220> FEATURE:
<221> NAME/KEY: VARIANT
<222> LOCATION: (4)...(4)
<223> OTHER INFORMATION: cyclohexylglycine

<400> SEQUENCE: 85

Xaa Ser Ser Xaa Gln Ser Val
1               5

<210> SEQ ID NO 86
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (1)...(1)
<223> OTHER INFORMATION: N-(PEG-2)-trans-4-hydroxyproline
<220> FEATURE:
<221> NAME/KEY: VARIANT
<222> LOCATION: (4)...(4)
<223> OTHER INFORMATION: cyclohexylglycine

<400> SEQUENCE: 86

Xaa Ala Ser Xaa Gln Ser Val
1               5

<210> SEQ ID NO 87
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (1)...(1)
<223> OTHER INFORMATION: N-(4-imidazolylacetyl)-trans-4-hydroxyproline

```
<220> FEATURE:
<221> NAME/KEY: VARIANT
<222> LOCATION: (4)...(4)
<223> OTHER INFORMATION: cyclohexylglycine

<400> SEQUENCE: 87

Xaa Ser Ser Xaa Gln Ser Val
 1               5

<210> SEQ ID NO 88
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: ACETYLATION
<222> LOCATION: (1)...(1)
<223> OTHER INFORMATION: N-acetyl-histidine
<220> FEATURE:
<221> NAME/KEY: VARIANT
<222> LOCATION: (4)...(4)
<223> OTHER INFORMATION: cyclohexylglycine

<400> SEQUENCE: 88

Xaa Ala Ser Xaa Gln Ser Val
 1               5

<210> SEQ ID NO 89
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (1)...(1)
<223> OTHER INFORMATION: N-(PEG-2)-cysteic acid
<220> FEATURE:
<221> NAME/KEY: VARIANT
<222> LOCATION: (4)...(4)
<223> OTHER INFORMATION: cyclohexylglycine

<400> SEQUENCE: 89

Xaa Ser Ser Xaa Gln Ser Val
 1               5

<210> SEQ ID NO 90
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (1)...(1)
<223> OTHER INFORMATION: N-gulonic-trans-4-hydroxyproline
<220> FEATURE:
<221> NAME/KEY: VARIANT
<222> LOCATION: (4)...(4)
<223> OTHER INFORMATION: cyclohexylglycine

<400> SEQUENCE: 90

Xaa Ser Ser Xaa Gln Ser Val
 1               5

<210> SEQ ID NO 91
<211> LENGTH: 7
<212> TYPE: PRT
<213> ORGANISM: Artificial Sequence
<220> FEATURE:
```

```
<223> OTHER INFORMATION: completely synthetic amino acid sequence
<220> FEATURE:
<221> NAME/KEY: VARIANT
<222> LOCATION: (1)...(1)
<223> OTHER INFORMATION: N-(4-phosphonylbutylryl)-trans-4-hydroxyproline
<220> FEATURE:
<221> NAME/KEY: VARIANT
<222> LOCATION: (4)...(4)
<223> OTHER INFORMATION: cyclohexylglycine

<400> SEQUENCE: 91

Xaa Ser Ser Xaa Gln Ser Val
 1               5

<210> SEQ ID NO 92
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (1)...(1)
<223> OTHER INFORMATION: N-cotinyl-trans-4-hydroxyproline
<220> FEATURE:
<221> NAME/KEY: VARIANT
<222> LOCATION: (4)...(4)
<223> OTHER INFORMATION: cyclohexylglycine

<400> SEQUENCE: 92

Xaa Ser Ser Xaa Gln Ser Val
 1               5

<210> SEQ ID NO 93
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (1)...(1)
<223> OTHER INFORMATION: N-(3-phosphonylpropionyl)-trans-4-
      hydroxyproline
<220> FEATURE:
<221> NAME/KEY: VARIANT
<222> LOCATION: (4)...(4)
<223> OTHER INFORMATION: cyclohexylglycine

<400> SEQUENCE: 93

Xaa Ser Ser Xaa Gln Ser Val
 1               5

<210> SEQ ID NO 94
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (1)...(1)
<223> OTHER INFORMATION: N-succinyl-trans-4-hydroxyproline
<220> FEATURE:
<221> NAME/KEY: VARIANT
<222> LOCATION: (4)...(4)
<223> OTHER INFORMATION: cyclohexylglycine

<400> SEQUENCE: 94

Xaa Ser Ser Xaa Gln Ser Val
 1               5
```

```
<210> SEQ ID NO 95
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (1)...(1)
<223> OTHER INFORMATION: N-glutaryl-trans-4-hydroxyproline
<220> FEATURE:
<221> NAME/KEY: VARIANT
<222> LOCATION: (4)...(4)
<223> OTHER INFORMATION: cyclohexylglycine

<400> SEQUENCE: 95

Xaa Ser Ser Xaa Gln Ser Val
 1               5

<210> SEQ ID NO 96
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (1)...(1)
<223> OTHER INFORMATION: N-ethoxysquarate-trans-4-hydroxyproline
<220> FEATURE:
<221> NAME/KEY: VARIANT
<222> LOCATION: (4)...(4)
<223> OTHER INFORMATION: cyclohexylglycine

<400> SEQUENCE: 96

Xaa Ser Ser Xaa Gln Ser Val
 1               5

<210> SEQ ID NO 97
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (1)...(1)
<223> OTHER INFORMATION: N-(PEG-2)-trans-4-hydroxyproline
<220> FEATURE:
<221> NAME/KEY: VARIANT
<222> LOCATION: (4)...(4)
<223> OTHER INFORMATION: cyclohexylglycine

<400> SEQUENCE: 97

Xaa Ser Ser Xaa Gln Ser Leu
 1               5

<210> SEQ ID NO 98
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: ACETYLATION
<222> LOCATION: (1)...(1)
<223> OTHER INFORMATION: N-acetylserine
<220> FEATURE:
<221> NAME/KEY: VARIANT
<222> LOCATION: (4)...(4)
<223> OTHER INFORMATION: cyclohexylglycine
```

-continued

```
<400> SEQUENCE: 98

Xaa Ser Ser Xaa Gln Ser Leu
 1               5

<210> SEQ ID NO 99
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: ACETYLATION
<222> LOCATION: (1)...(1)
<223> OTHER INFORMATION: N-acetylserine
<220> FEATURE:
<221> NAME/KEY: VARIANT
<222> LOCATION: (4)...(4)
<223> OTHER INFORMATION: cyclohexylglycine

<400> SEQUENCE: 99

Xaa Ser Ser Xaa Gln Ser Leu
 1               5

<210> SEQ ID NO 100
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (1)...(1)
<223> OTHER INFORMATION: N-glutaryl-trans-4-hydroxyproline
<220> FEATURE:
<221> NAME/KEY: VARIANT
<222> LOCATION: (4)...(4)
<223> OTHER INFORMATION: cyclohexylglycine

<400> SEQUENCE: 100

Xaa Ala Ser Xaa Gln Ser Leu
 1               5

<210> SEQ ID NO 101
<211> LENGTH: 5
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: ACETYLATION
<222> LOCATION: (1)...(1)
<223> OTHER INFORMATION: N-acetylserine
<220> FEATURE:
<221> NAME/KEY: VARIANT
<222> LOCATION: (4)...(4)
<223> OTHER INFORMATION: cyclohexylglycine

<400> SEQUENCE: 101

Xaa Xaa Gln Ser Leu
 1               5

<210> SEQ ID NO 102
<211> LENGTH: 6
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: ACETYLATION
<222> LOCATION: (1)...(1)
<223> OTHER INFORMATION: N-acetylserine
```

-continued

```
<220> FEATURE:
<221> NAME/KEY: VARIANT
<222> LOCATION: (3)...(3)
<223> OTHER INFORMATION: cyclohexylglycine

<400> SEQUENCE: 102

Xaa Ser Xaa Gln Ser Leu
 1               5

<210> SEQ ID NO 103
<211> LENGTH: 7
<212> TYPE: PRT
<213> ORGANISM: Artificial Sequence
<220> FEATURE:
<223> OTHER INFORMATION: completely synthetic amino acid sequence
<220> FEATURE:
<221> NAME/KEY: VARIANT
<222> LOCATION: (1)...(1)
<223> OTHER INFORMATION: N-acetyl-beta-keto-4-hydroxyproline
<220> FEATURE:
<221> NAME/KEY: VARIANT
<222> LOCATION: (4)...(4)
<223> OTHER INFORMATION: cyclohexylglycine

<400> SEQUENCE: 103

Xaa Ala Ser Xaa Gln Ser Leu
 1               5
```